(12) United States Patent
Langlois et al.

(10) Patent No.: US 6,423,870 B1
(45) Date of Patent: Jul. 23, 2002

(54) TRICYCLIC COMPOUNDS, PREPARATION METHOD AND PHARMACEUTICAL COMPOSITIONS CONTAINING SAME

(75) Inventors: Michel Langlois, Sceaux; Monique Mathe-Allainmat, Massy; Carole Jellimann, Paris; Jean Andrieux, Antony; Caroline Bennejean, Charenton le Pont; Pierre Renard, Le Chesnay; Philippe Delagrange, Issy les Moulineaux, all of (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 0 days.

(21) Appl. No.: 09/600,373
(22) PCT Filed: Dec. 11, 1998
(86) PCT No.: PCT/FR98/02694
    § 371 (c)(1),
    (2), (4) Date: Jul. 14, 2000
(87) PCT Pub. No.: WO99/36392
    PCT Pub. Date: Jul. 22, 1999

(30) Foreign Application Priority Data

Jan. 16, 1998 (FR) ............................................. 98 00424

(51) Int. Cl.[7] ........................ C07C 233/05; A61K 31/16
(52) U.S. Cl. ........................ 564/219; 514/337; 514/339; 514/411; 514/443; 514/463; 514/585; 514/613; 514/623; 514/627; 514/628; 514/629; 514/630; 548/436; 548/437; 548/438; 549/43; 549/44; 549/45; 549/47; 549/458; 564/26; 564/47; 564/48; 564/56; 564/74; 564/123; 564/173; 564/172; 564/180; 564/182; 564/183; 564/207; 564/211; 564/221
(58) Field of Search ................... 514/585, 623, 514/613, 630, 629, 628, 627, 411, 337, 339, 443, 468, 624, 625; 564/182, 180, 183, 172, 207, 173, 211, 219, 221, 26, 47, 48, 56, 74, 123; 549/43, 44, 45, 47, 458; 548/436, 437, 438

(56) References Cited

U.S. PATENT DOCUMENTS 5,712,312 A * 1/1998 Langlois et al. ............. 514/585
5,849,781 A * 12/1998 Langlois et al. ............. 514/411

FOREIGN PATENT DOCUMENTS

| EP | 0708099 | 4/1996 |
| EP | 737670 | 10/1996 |
| EP | 0745584 | 12/1996 |
| WO | WO9529173 | 11/1995 |
| WO | WO 9608466 | 3/1996 |
| WO | WO97/32871 | 9/1997 |

* cited by examiner

*Primary Examiner*—Shailendra Kumar
(74) *Attorney, Agent, or Firm*—The Firm of Hueschen and Sage; G. Patrick Sage

(57) ABSTRACT

The invention concerns compounds of formula (I) in which: A forms a tricyclic system of formula $A_1$, $A_2$, $A_3$ or $A_4$; $R^1$ represents a hydrogen atom, an alkyl, hydroxy, alkoxy or oxo group; $(R^2)_m$ and $(R^3)_{m'}$ are such as defined in the description; n represents an integer such that $0 \leq n \leq 3$; p represents an integer such as defined in the description; B represents a group (a) or (b). The invention is useful for preparing medicines.

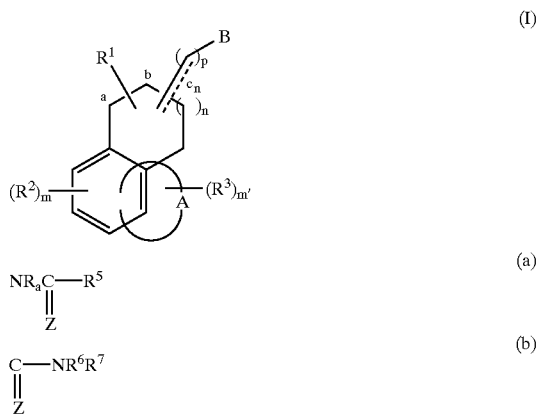

31 Claims, No Drawings

TRICYCLIC COMPOUNDS, PREPARATION METHOD AND PHARMACEUTICAL COMPOSITIONS CONTAINING SAME

The prsent application is a U.S. National Application filed under 35 USC 371 of PCT/FR98/02694 filed Dec. 11, 1998, based upon French application Serial No. 98.00424 filed Jan. 16, 1998.

FIELD OF THE INVENTION

The present invention relates to new tricyclic compounds.

DESCRIPTION OF THE PRIOR ART

There are known from the prior art 2,3-dihydrophenalene compounds (J. Chem. Soc. C, 1971, 9, pp1607–1609) which are described as synthesis intermediates, and 1,3,4,5-tetrahydrobenzo[cd]indole compounds (EP 353 557) for use in the preparation of platelet aggregation inhibitors.

Moreover, Application EP 737 670 describes tricyclic amide compounds as melatoninergic receptor ligands.

BACKGROUND OF THE INVENTION

Numerous studies in the last ten years have demonstrated the key role of melatonin (N-acetyl-5-methoxytryptamine) in many physiopathological phenomena and in the control of the circadian rhythm. Its half-life is quite short, however, owing to the fact that it is rapidly metabolised. Great interest therefore lies in the possibility of providing the clinician with melatonin analogues that are metabolically more stable, have an agonist or antagonist character and may be expected to have a therapeutic effect that is superior to that of the hormone itself.

In addition to their beneficial action on circadian rhythm disorders (J. Neurosurg. 1985, 63, pp 321–341) and sleep disorders (Psychopharmacology, 1990, 100, pp 222–226), ligands of the melatoninergic system have valuable pharmacological properties in respect of the central nervous system, especially anxiolytic and antipsychotic properties (Neuropharmacology of Pineal Secretions, 1990, 8 (3-4), pp 264–272) and analgesic properties (Pharmacopsychiat., 1987, 20, pp 222–223) as well as for the treatment of Parkinson's disease (J. Neurosurg. 1985, 63, pp 321–341) and Alzheimer's disease (Brain Research, 1990, 528. pp 170–174). Those compounds have also demonstrated activity in respect of certain cancers (Melatonin—Clinical Perspectives, Oxford University Press, 1988, pp 164–165), ovulation (Science 1987, 227, pp 714–720), diabetes (Clinical Endocrinology, 1986, 24, pp 359–364), and in the treatment of obesity (International Journal of Eating Disorders, 1996, 20 (4), pp 443–446).

Those various effects are exerted via the intermediary of specific melatonin receptors. Molecular biology studies have demonstrated the existence of a number of receptor subtypes that are capable of binding that hormone (Trends Pharmacol. Sci., 1995, 16, p. 50; WO 97.04094). It has been possible for various species, including mammals, for some of those receptors to be located and characterised. In order to be able to understand the physiological functions of those receptors better, it is of great advantage to have available specific ligands. Moreover, such compounds, by interacting selectively with one or other of those receptors, may be excellent medicaments for the clinician in the treatment of pathologies associated with the melatoninergic system, some of which have been mentioned above.

The compounds of the present invention are new and have very strong affinity for melatonin receptors and/or selectivity for one or other of the melatoninergic receptor sub-types.

DETAILED DESCRIPTION OF THE INVENTION

The present invention relates more especially to compounds of formula (I)

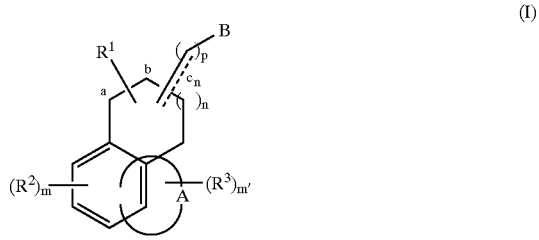

wherein:

A forms with the group to which it is bonded a tricyclic system selected from $A_1$, $A_2$, $A_3$ and $A_4$:

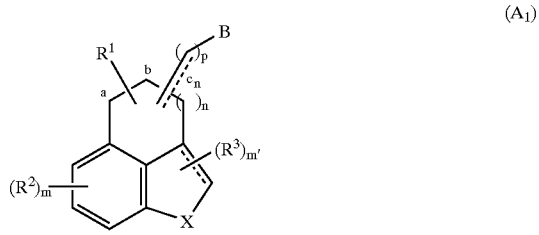

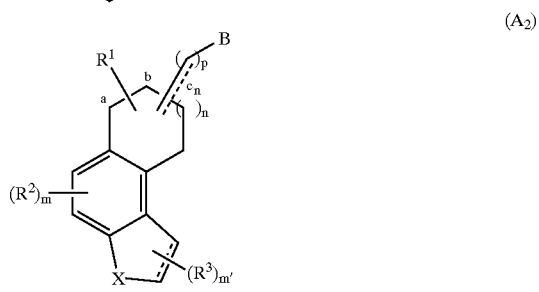

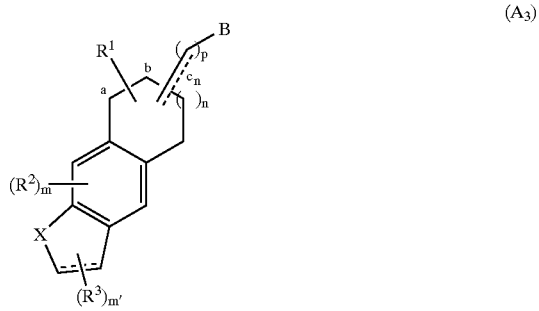

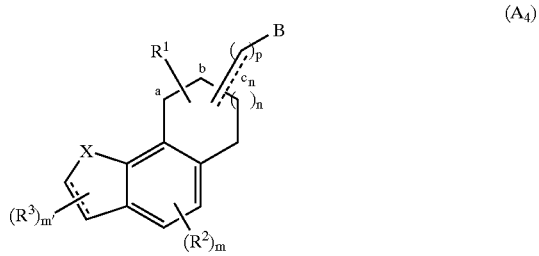

$R^1$ represents a hydrogen atom, a halogen atom or a linear or branched ($C_1$–$C_6$)alkyl, linear or branched ($C_1$–$C_6$) alkoxy, hydroxy or oxo group, $R^2$ and $R^3$, which may be the same or different, represent a halogen atom or an $R_a$, $OR_a$, $COR_a$, $OCOR_a$ or COOR$_a$ group (wherein R$_a$ represents a hydrogen atom, an optionally substituted linear or branched (C$_1$–C$_6$)alkyl group, linear or branched (C$_1$–C$_6$) trihaloalkyl, an optionally substituted linear or branched (C$_2$–C$_6$)alkenyl group, an optionally substituted linear or branched (C$_2$–C$_6$)alkynyl group, an optionally substituted (C$_3$–C$_8$)cycloalkyl group, an optionally substituted (C$_3$–C$_8$)cycloalkyl-(C$_1$–C$_6$)alkyl group in which the alkyl moiety is linear or branched, or an optionally substituted aryl group), the symbols (R$^2$)$_m$ and (R$^3$)$_{m'}$ denote that the ring in question may be substituted by from 1 to 3 groups (which may be the same or different) belonging to the definitions for R$^2$ and R$^3$, X, when A represents a tricyclic system A$_1$, A$_2$, A$_3$ or A$_4$, represents a sulphur atom, a (CH$_2$)$_q$ group (wherein q is 1 or 2), a —CH=CH— group, or an NR$^4$ group (wherein R$^4$ represents a hydrogen atom or an optionally substituted linear or branched (C$_1$–C$_6$)alkyl group), or X represents an oxygen atom when A represents the tricyclic system A$_1$, n is an integer such that 0≦n≦3 p is an integer such that 1≦p≦3 when n is 1, 2 or 3 and the

chain is in the b position and A represents either a group A$_2$, A$_3$ or A$_4$ wherein X represents a —CH=CH— group, or a group A$_1$, and such that 0≦p≦3 in all other cases, it being possible for the

chain to be unsubstituted or substituted by one or more groups, which may be the same or different, selected from R$_a$, OR$_a$, COR$_a$, COOR$_a$ or halogen atoms, B represents:

an

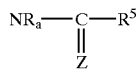

group wherein R$_a$ is as defined hereinbefore, Z represents an oxygen atom or a sulphur atom, and R$^5$ represents an R$_a$ group or an NR$^6$R$^7$ group wherein R$^6$ and R$^7$, which may be the same or different, represent an R$_a$ group, or a

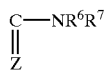

group wherein Z, R$^6$ and R$^7$ are as defined hereinbefore, the symbol ⋯ denotes that the bond may be single or double provided that the valency of the atoms is respected, it being understood that the symbol

is used to denote the formula

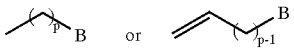

(in which case p is other than 0), with the proviso that:

when the tricyclic group of formula A$_1$ is a 6-methoxytetrahydrobenzo[cd]indole, B cannot represent an NHCOMe group, the compound of formula (I) cannot represent N-(4-methyl-2,3-dihydro-1H-1-phenalenyl)-1-cyclopropanecarboxamide, N-(4-methyl-2,3-dihydro-1H-1-phenalenyl)-2-chloroacetamide, 2-methyl-1,3,4,5-tetrahydrobenzo[cd]indole-3-carboxamide, N-(5-hydroxy-1,2,2a,3,4,5-hexahydro-4-acenaphthylenyl)acetamide, N-(5-hydroxy-1,2,2a,3,4,5-hexahydro-4-acenaphthylenyl)benzamide or N-(1,2,2a,3,4,5-hexahydro-4-acenaphthylenyl)acetamide, it being understood that:

"aryl" is used to denote a phenyl or naphthyl group each optionally substituted by one or more groups, which may be the same or different, selected from hydroxy, linear or branched (C$_1$–C$_6$)-alkoxy, linear or branched (C$_1$–C$_6$)alkyl, cyano, nitro, amino, trihaloalkyl, or halogen atoms, the expression "optionally substituted" applied to the terms "alkyl", "alkenyl" and "alkynyl" denotes that those groups may be substituted by one or more groups, which may be the same or different, selected from hydroxy, linear or branched (C$_1$–C$_6$)alkoxy, aryl, or halogen atoms, the expression "optionally substituted" applied to the terms "cycloalkyl" and "cycloalkylalkyl" denotes that the cyclic moiety may be substituted by one or more groups selected from hydroxy, linear or branched (C$_1$–C$_6$)alkoxy, oxo, or halogen atoms, their enantiomers and diastereoisomers, and addition salts thereof with a pharmaceutically acceptable acid or base.

Amongst the pharmaceutically acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid, etc.

Amongst the pharmaceutically acceptable bases there may be mentioned by way of non-limiting example sodium hydroxide, potassium hydroxide, triethylamine, tert-butylamine, etc.

An advantageous embodiment of the present invention relates to compounds of formula (I) represented by formula (I$_A$):

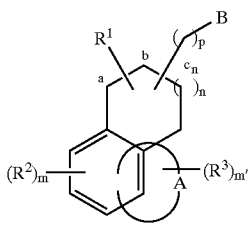

(I_A)

wherein:
A forms with the group to which it is bonded a tricyclic system selected from $A'_1$, $A'_2$, $A'_3$ and $A'_4$:

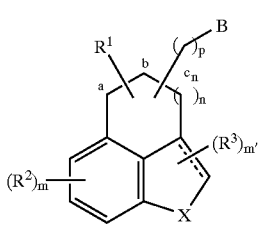

(A'_1)

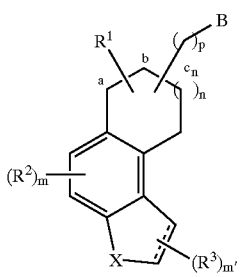

(A'_2)

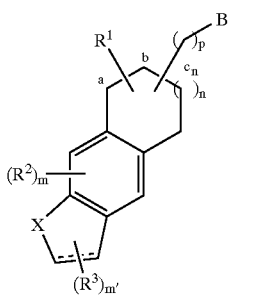

(A'_3)

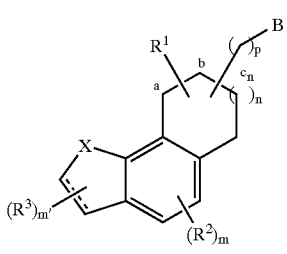

(A'_4)

$R^1$ represents a hydrogen atom, a halogen atom or a linear or branched ($C_1$–$C_6$)alkyl, linear or branched ($C_1$–$C_6$) alkoxy, hydroxy or oxo group, $R^2$ and $R^3$, which may be the same or different, represent a halogen atom or an $R_a$, $OR_a$, $COR_a$, $OCOR_a$ or $COOR_a$ group (wherein $R_a$ represents a hydrogen atom, an optionally substituted linear or branched ($C_1$–$C_6$)alkyl group, linear or branched ($C_1$–$C_6$) trihaloalkyl, an optionally substituted linear or branched ($C_2$–$C_6$)alkenyl group, an optionally substituted linear or branched ($C_2$–$C_6$)alkynyl group, an optionally substituted ($C_3$–$C_8$)cycloalkyl group, an optionally substituted ($C_3$–$C_8$)cycloalkyl-($C_1$–$C_6$)alkyl group in which the alkyl moiety is linear or branched, or an optionally substituted aryl group), the symbols $(R^2)_m$ and $(R^3)_{m'}$ denote that the ring in question may be substituted by from 1 to 3 groups (which may be the same or different) belonging to the definitions for $R^2$ and $R^3$, X, when A represents a tricyclic system $A'_1$, $A'_2$, $A'_3$ or $A'_4$, represents a sulphur atom, a $(CH_2)_q$ group (wherein q is 1 or 2), a —CH=CH— group, or an $NR^4$ group (wherein $R^4$ represents a hydrogen atom or an optionally substituted linear or branched ($C_1$–$C_6$)alkyl group), or X represents an oxygen atom when A represents the tricyclic system $A'_1$, n is an integer such that $0 \leq n \leq 3$ p is an integer such that $1 \leq p \leq 3$ when n is 1, 2 or 3 and the —$(CH_2)_p$—B chain is in the b 20 position and A represents either a group $A'_2$, $A'_3$ or $A'_4$ wherein X represents a —CH=CH— group, or a group $A'_1$, and such that $0 \leq p \leq 3$ in all other cases, it being possible for the $(CH_2)_p$ chain to be unsubstituted or substituted by one or more groups, which may be the same or different, selected from $R_a$, $OR_a$, $COR_a$, $COOR_a$ or halogen atoms, B represents:

an

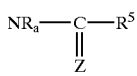

group wherein $R_a$ is as defined hereinbefore, Z represents an oxygen atom or a sulphur atom, and $R^5$ represents an $R_a$ group or an $NR^6R^7$ group wherein $R^6$ and $R^7$, which may be the same or different, represent an $R_a$ group, or a

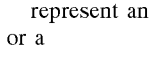

group wherein Z, $R^6$ and $R^7$ are as defined hereinbefore, the symbol ....... denotes that the bond may be single or double provided that the valency of the atoms is respected, with the proviso that:
when the tricyclic group of formula $A'_1$ is a 6-methoxytetrahydrobenzo[cd]indole, B cannot represent an NHCOMe group, the compound of formula (I) cannot represent N-(4-methyl-2,3-dihydro-1H-1-phenalenyl)-1-cyclopropanecarboxamide, N-(4-methyl-2,3-dihydro-1H-1-phenalenyl)-2-chloroacetamide, 2-methyl-1,3,4,5-tetrahydrobenzo[cd]indole-3-carboxamide, N-(5-hydroxy-1,2,2a,3,4,5-hexahydro-4-acenaphthylenyl)acetamide, N-(5-hydroxy-1,2,2a,3,4,5-hexahydro-4-acenaphthylenyl)

benzamide or N-(1,2,2a,3,4,5-hexahydro-4-acenaphthylenyl)acetamide, it being understood that:

"aryl" is used to denote a phenyl or naphthyl group each optionally substituted by one or more groups, which may be the same or different, selected from hydroxy, linear or branched $(C_1-C_6)$alkoxy, linear or branched $(C_1-C_6)$alkyl, cyano, nitro, amino, trihaloalkyl, or halogen atoms, the expression "optionally substituted" applied to the terms "alkyl", "alkenyl" and "alkynyl" denotes that those groups may be substituted by one or more groups, which may be the same or different, selected from hydroxy, linear or branched $(C_1-C_6)$alkoxy, aryl, or halogen atoms, the expression "optionally substituted" applied to the terms "cycloalkyl" and "cycloalkylalkyl" denotes that the cyclic moiety may be substituted by one or more groups, which may be the same or different, selected from hydroxy, linear or branched $(C_1-C_6)$ alkoxy, oxo, or halogen atoms, their enantiomers and diastereoisomers, and addition salts thereof with a pharmaceutically acceptable acid or base.

A further advantageous embodiment of the present invention relates to compounds of formula (I) represented by formula ($I_B$):

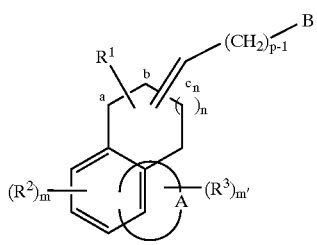

(I$_B$)

wherein

A forms with the group to which it is bonded a tricyclic system selected from A"$_1$, A"$_2$, A"$_3$ and A"$_4$:

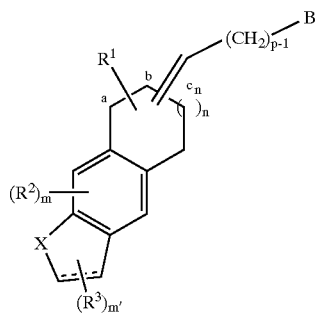

(A"$_1$)

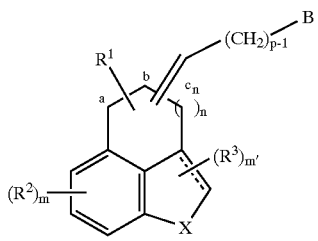

(A"$_2$)

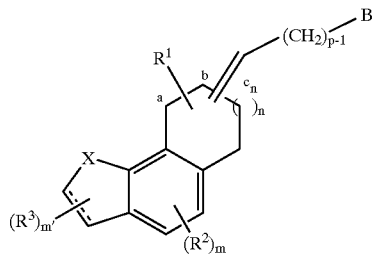

(A"$_3$)

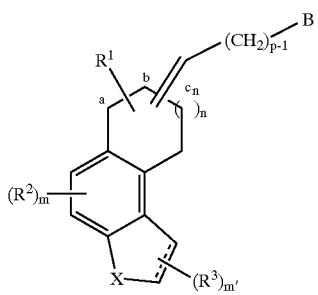

(A"$_4$)

$R^1$ represents a hydrogen atom, a halogen atom or a linear or branched $(C_1-C_6)$alkyl, linear or branched $(C_1-C_6)$ alkoxy, hydroxy or oxo group, $R^2$ and $R^3$, which may be the same or different, represent a halogen atom or an $R_a$, $OR_a$, $COR_a$, $OCOR_a$ or $COOR_a$ group (wherein $R_a$ represents a hydrogen atom, an optionally substituted linear or branched $(C_1-C_6)$alkyl group, linear or branched $(C_1-C_6)$ trihaloalkyl, an optionally substituted linear or branched $(C_2-C_6)$alkenyl group, an optionally substituted linear or branched $(C_2-C_6)$alkynyl group, an optionally substituted $(C_3-C_8)$cycloalkyl group, an optionally substituted $(C_3-C_8)$cycloalkyl-$(C_1-C_6)$alkyl group in which the alkyl moiety is linear or branched, or an optionally substituted aryl group), the symbols $(R^2)_m$ and $(R^3)_{m'}$ denote that the ring in question may be substituted by from 1 to 3 groups (which may be the same or different) belonging to the definitions for $R^2$ and $R^3$, X, when A represents a tricyclic system A"$_1$, A"$_2$, A"$_3$ or A"$_4$, represents a sulphur atom, a $(CH_2)_q$ group (wherein q is 1 or 2), a —CH=CH— group, or an NR$^4$ group (wherein R$^4$ represents a hydrogen atom or an optionally substituted linear or branched $(C_1-C_6)$-alkyl group), or X represents an oxygen atom when A represents the tricyclic system A"$_1$, n is an integer such that $0 \leq n \leq 3$ p is an integer such that $1 \leq p \leq 3$ it being possible for the

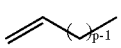

chain to be unsubstituted or substituted by one or more groups, which may be the same or different, selected from $R_a$, $OR_a$, $COR_a$, $COOR_a$ or halogen atoms, B represents:

an $$NR_a-\underset{\underset{Z}{\parallel}}{C}-R^5$$

group wherein $R_a$ is as defined hereinbefore, Z represents an oxygen atom or a sulphur atom, and $R^5$ represents an $R_a$ group or an $NR^6R^7$ group wherein $R^6$ and $R^7$, which may be the same or different, represent an $R_a$ group,
or a $$\underset{\underset{Z}{\parallel}}{C}-NR^6R^7$$

group wherein Z, $R^6$ and $R^7$ are as defined hereinbefore,
the symbol ⋯⋯ denotes that the bond may be single or double provided that the valency of the atoms is respected,
it being understood that:
"aryl" is used to denote a phenyl or naphthyl group each optionally substituted by one or more groups, which may be the same or different, selected from hydroxy, linear or branched ($C_1$–$C_6$)alkoxy, linear or branched ($C_1$–$C_6$)alkyl, cyano, nitro, amino, trihaloalkyl, or halogen atoms,
the expression "optionally substituted" applied to the terms "alkyl", "alkenyl" and "alkynyl" denotes that those groups may be substituted by one or more groups, which may be the same or different, selected from hydroxy, linear or branched ($C_1$–$C_6$)alkoxy, aryl, or halogen atoms,
the expression "optionally substituted" applied to the terms "cycloalkyl" and "cycloalkylalkyl" denotes that the cyclic moiety may be substituted by one or more groups, which may be the same or different, selected from hydroxy, linear or branched ($C_1$–$C_6$) alkoxy, oxo, or halogen atoms,
their enantiomers and diastereoisomers, and addition salts thereof with a pharmaceutically acceptable acid or base.

The preferred compounds of the invention are those wherein A forms with the groups to which it is bonded a tricyclic system of formula $A_1$.

The preferred values for n are 0, 1 and 2.

More especially, the invention relates to compounds wherein A forms with the groups to which it is bonded a tricyclic system of formula Al wherein X represents a $(CH_2)_q$ group (wherein q is as defined hereinbefore) or a —CH═CH— group, such as, for example, a 2,3-dihydrophenalene, 1,2-dihydroacenaphthylene or 7,8,9,10-tetrahydrocyclohepta[de]naphthalene tricyclic system.

The preferred values for p are 0, 1 and 2.

The preferred substituents $R^2$ and $R^3$ of the invention are a hydrogen atom and alkoxy and alkyl groups.

The preferred $R^1$ group of the invention is a hydrogen atom.

Advantageously, the invention relates to compounds substituted by the $$\cdots\cdots(\phantom{x})_p^{B}$$

chain in the a or c position and more especially to those compounds wherein p represents an integer 0 (in which case the bond ⋯⋯ is single), 1 or 2.

The preferred B groups of the invention are the $NHCOR^5$ group wherein $R^5$ is as defined hereinbefore (such as, for example, alkyl, alkenyl, alkynyl, cycloalkyl, cycloalkylalkyl, aryl or arylalkyl groups),
and the $CONHR^6$ group wherein $R^6$ is as defined hereinbefore (such as, for example, alkyl, alkenyl, alkynyl, cycloalkyl, cycloalkylalkyl, aryl or arylalkyl groups).

More advantageously, the invention relates to the 2,3-dihydrophenalene, 1,2-dihydroacenaphthylene or 7,8,9,10-tetrahydrocyclohepta[de]naphthalene tricyclic systems, each unsubstituted or substituted on the naphthalene moiety by one or more alkoxy or alkyl groups, and substituted in the a or c position by a $$\cdots\cdots(\phantom{x})_p^{B}$$

group wherein B represents an $NHCOR^5$ or $CONHR^6$ group (wherein $R^5$ and $R^6$ are as defined hereinbefore).

More especially, the invention relates to the 1,2-dihydroacenaphthylene or 7,8,9,10-tetrahydrocyclohepta [de]naphthalene tricyclic systems,
each unsubstituted or substituted on the naphthalene moiety by one or two alkoxy groups (for example a methoxy group), and substituted in the a or c position by a ═CH—B, ═CH—$CH_2$—B, —B, —$CH_2$—B or —$(CH_2)_2$—B group wherein B represents an $NHCOR^5$ or $CONHR^6$ group wherein $R^5$ and $R^6$ represent an alkyl, alkenyl, alkynyl, trihaloalkyl, cycloalkyl, cycloalkylalkyl, aryl or arylalkyl group, such as, for example, methyl, ethyl, propyl, isopropyl, butyl, pentyl, hexyl, vinyl, propargyl, trifluoromethyl, cyclopropyl, cyclobutyl, cyclopentyl, cyclohexyl, phenyl, naphthyl or benzyl.

Very advantageously, the invention relates to 2,3-dihydrophenalene compounds, unsubstituted or substituted on the naphthalene moiety by one or two alkoxy groups (for example a methoxy group),
and substituted in the a or c position by a ═CH—B, ═CH—$CH_2$—B, —$CH_2$—B or —$(CH_2)_2$—B group wherein B represents an $NHCOR^5$ or $CONHR^6$ group wherein $R^5$ and $R^6$ represent an alkyl, alkenyl, alkynyl, trihaloalkyl, cycloalkyl, cycloalkylalkyl, aryl or arylalkyl group, such as, for example, methyl, ethyl, propyl, isopropyl, butyl, pentyl, hexyl, vinyl, propargyl, trifluoromethyl, cyclopropyl, cyclobutyl, cyclopentyl, cyclohexyl, phenyl, naphthyl or benzyl.

Even more advantageously, the invention relates to N-[(4-methoxy-2,3-dihydro-1H-1-phenalenyl)methyl]acetamide, N-[(4-methoxy-2,3-dihydro-1H-phenalenyl)methyl] propionamide, N-[(4-methoxy-2,3-dihydro-1H-1-phenalenyl)methyl]cyclopropanecarboxamide, N-[(4-methoxy-2,3-dihydro-1H-1-phenalenyl)methyl]butanamide, N-[2-(4-methoxy-2,3-dihydro-1H-1-phenalenyl)ethyl] acetamide, N-[2-(4-methoxy-2,3-dihydro-1H-1-phenalenyl) ethyl]propanamide, N-[2-(4-methoxy-2,3-dihydro-1H-1-phenalenyl)ethyl]-1-cyclopropanecarboxamide, N-(8-methoxy-1,2-dihydro-1-acenaphthylenyl)acetamide, N-[(4-methoxy-2,3-dihydro-1H-1-phenalenyl)methyl]butanamide, N-[2-(9-methoxy-2,3-dihydro-1H-1-phenalenyl)ethyl] acetamide, N-[2-(9-methoxy-2,3-dihydro-1H-1-phenalenyl) ethyl]butanamide, N-[2-(4-methoxy-2,3-dihydro-1H-1-phenalenyl)ethyl]butanamide, N-[2-(4,9-dimethoxy-2,3-dihydro-1H-1-phenalenyl)ethyl]propanamide, N-[2-(4,9-dimethoxy-2,3-dihydro-1H-1-phenalenyl)ethyl]butanamide, N-[2-(4,9-dimethoxy-2,3-dihydro-1H-1-phenalenyl)ethyl]-1-cyclopropanecarboxamide, N-[2-(4,9-dimethoxy-2,3- dihydro-1H-1-phenalenyl)ethyl]acetamide, N-[2-(9-methoxy-2,3-dihydro-1H-1-phenalenyl)methyl]-acetamide, N-[2-(9-methoxy-2,3-dihydro-1H-1-phenalenyl)methyl] butanamide, N-[2-(4,9-dimethoxy-2,3-dihydro-1H-1-phenalenyl)methyl]acetamide, N-[2-(4,9-dimethoxy-2,3-dihydro-1H-1-phenalenyl)methyl]propanamide, N-[2-(4,9-dimethoxy-2,3-dihydro-1H-1-phenalenyl)methyl] butanamide, N-[2-(4,9-dimethoxy-2,3-dihydro-1H-1-phenalenyl)-methyl]-1-cyclopropanecarboxamide, (E)-N-methyl-2-(4-methoxy-2,3-dihydro-1H-1-phenalenylidene) acetamide, (Z)-N-methyl-2-(4-methoxy-2,3-dihydro-1H-1-phenalenylidene)acetamide, N-(1,2-dihydro-1-acenaphthylenylmethyl)acetamide, N-(1,2-dihydro-1-acenaphthylenylmethyl)propanamide, N-(1,2-dihydro-1-acenaphthylenylmethyl)butanamide, N-(1,2-dihydro-1-acenaphthylenylmethyl-1-cyclopropane-carboxamide, N-(8-methoxy-1,2-dihydro-1-acenaphthylmethyl) acetamide, N-(8-methoxy-1,2-dihydro-1-acenaphthyl-methyl)propanamide, N-(8-methoxy-1,2-dihydro-1-acenaphthylmethyl)-1-cyclopropanecarboxamide, N-(8-methoxy-1,2-dihydro-1-acenaphthylmethyl)butanamide, N-[2-(1,2-dihydro-1-acenaphthyl)ethyl]acetamide, N-[2-(1,2-dihydro-1-acenaphthyl)ethyl]propanamide, N-[2-(1,2-dihydro-1-acenaphthyl)ethyl]butanamide, N-[2-(1,2-dihydro-1-acenaphthyl)ethyl]cyclopropanecarboxamide, N-[2-(8-methoxy-1,2-dihydro-1-acenaphthyl)ethyl] acetamide, N-[2-(8-methoxy-1,2-dihydro-1-acenaphthyl) ethyl]propanamide, N-[2-(8-methoxy-1,2-dihydro-1-acenaphthyl)ethyl]butanamide, N-[2-(8-methoxy-1,2-dihydro-1-acenaphthyl)ethyl]-1-cyclopropanecarboxamide, N-[2-(1-methoxy-7,8,9,10-tetrahydrocyclohepta[de] naphthalen-7-ylidene)ethyl]propanamide.

The enantiomers and diastereoisomers of the preferred compounds of the invention and addition salts thereof with a pharmaceutically acceptable acid or base form an integral part of the present invention.

The invention relates also to a process for the preparation of the compounds of formula (I) wherein A forms with the groups to which it is bonded a tricyclic system of formula ($A_1$), which process is characterised in that there is used as starting material a compound of formula (II):

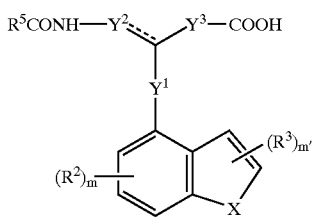

(II)

wherein $R^2$, $R^3$, $R^5$, X, m, m' and the symbol ....... are as defined hereinbefore, $Y^2$ represents a $(CH_2)_q$ group (wherein q is 1, 2 or 3, or q is 0 when the symbol ....... is a single bond), $Y^1$ represents a $(CH_2)_{q'}$ group (wherein q' is 0, 1, 2 or 3), substituted by an $R^1$ group as defined hereinbefore, $Y^3$ represents a $(CH_2)_{q''}$ group (wherein q" is 0, 1, 2 or 3), substituted by an $R^1$ group as defined hereinbefore, where q'+q"≦3 and $R^1$ must represent a hydrogen atom in at least one of the two groups $Y^1$ and $Y^3$, which is cyclised in a basic medium to yield a compound of formula (III):

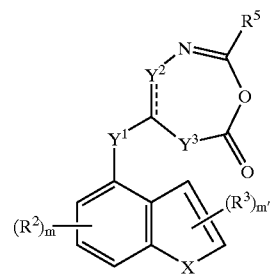

(III)

wherein $R^2$, $R^3$, $R^5$, X, $Y^1$, $Y^2$, $Y^3$, m, m' and the symbol ....... as defined hereinbefore,
which is then reacted with a Lewis acid to obtain a compound of formula (I/a), which is a particular case of the compounds of formula (I):

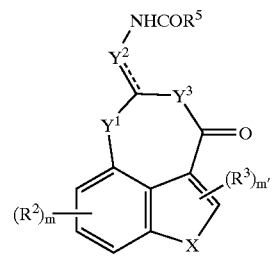

(I/a)

wherein $R^2$, $R^3$, $R^5$, X, $Y^1$, $Y^2$, $Y^3$, m, m' and the symbol ....... are as defined hereinbefore, which is then reduced to obtain a compound of formula (I/b), which is a particular case of the compounds of formula (I):

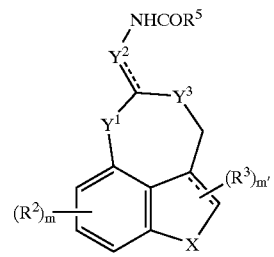

(I/b)

wherein $R^2$, $R^3$, $R^5$, X, $Y^1$, $Y^2$, $Y^3$, m, m' and the symbol ....... are as defined hereinbefore,
or a compound of formula (IV):

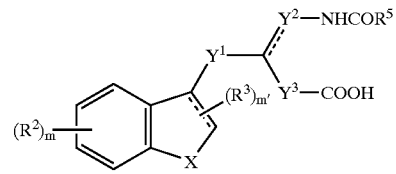

(IV)

wherein $R^2$, $R^3$, $R^5$, X, $Y^1$, $Y^2$, $Y^3$, m, m' and the symbol ....... are as defined hereinbefore,
which is successively
  cyclised
  reacted with a Lewis acid
to yield a compound of formula (I/c), which is a particular case of the compounds of formula (I):

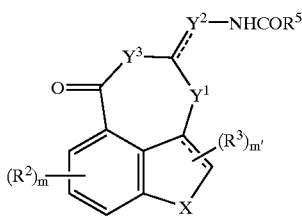

(I/c)

wherein $R^2$, $R^3$, $R^5$, X, $Y^1$, $Y^2$, $Y^3$, m, m' and the symbols ⋯⋯ are as defined hereinbefore, which is reduced to obtain a compound of formula (I/d), which is a particular case of the compounds of formula (I):

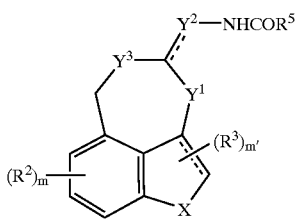

(I/d)

wherein $R^2$, $R^3$, $R^5$, X, $Y^1$, $Y^2$, $Y^3$, m, m' and the symbol ⋯⋯ are as defined hereinbefore,
the totality of the compounds (I/a), (I/b), (I/c) and (I/d) constituting the compounds of formula (I/e), a particular case of the compounds of formula (I):

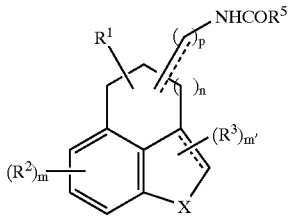

(I/e)

wherein $R^1$, $R^2$, $R^3$, $R^5$, n, p, X, m, m' and the symbol ⋯⋯ are as defined hereinbefore,
which is either:
  subjected to the action of a compound of formula (V): $R'_a$—W (V) wherein $R'_a$ may have any of the meanings of the $R_a$ group as defined hereinbefore with the exception of a hydrogen atom, and W represents a leaving group, such as a halogen atom or a tosyl group, to yield a compound of formula (I/f), which is a particular case of the compounds of formula (I):

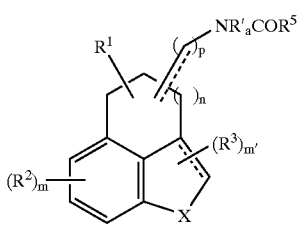

(I/f)

wherein $R^1$, $R^2$, $R^3$, $R^5$, $R'_a$, n, p, X, m, m' and the symbol ⋯⋯ are as defined hereinbefore, the totality of the compounds of formulae (I/e) and (I/f) constituting the compounds of formula (I/g):

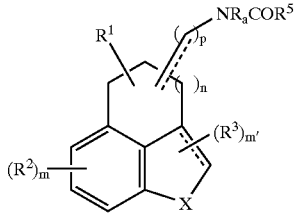

(I/g)

wherein $R^1$, $R^2$, $R^3$, $R^5$, $R_a$, n, p, X, m, m' and the symbol ⋯⋯ are as defined hereinbefore, which may be subjected to the action of a thionisation agent, such as Lawesson's reagent, to obtain a compound of formula (I/h), which is a particular case of the compounds of formula (I):

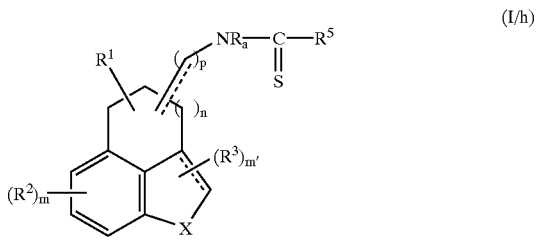

(I/h)

wherein $R^1$, $R^2$, $R^3$, $R^5$, $R_a$, n, p, X, m, m' and the symbol ⋯⋯ are as defined hereinbefore, or hydrolysed in a basic medium to yield a compound of formula (VI):

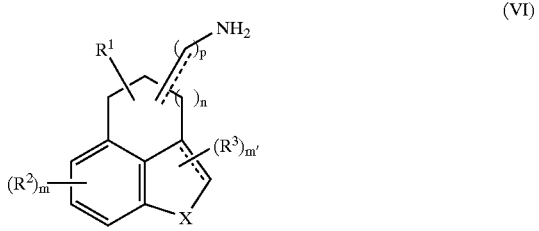

(VI)

wherein $R^1$, $R^2$, $R^3$, n, p, X, m, m' and the symbol ⋯⋯ are as defined hereinbefore,
which is either:
  subjected to the action of a pyrylium salt to yield a compound of formula (VII):

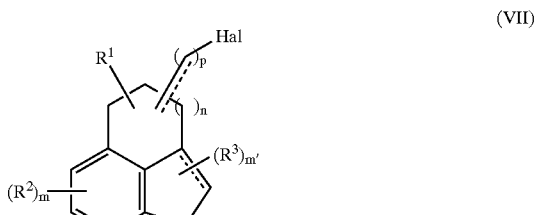

(VII)

wherein Hal represents a halogen atom and $R^1$, $R^2$, $R^3$, n, p, X, m, m' and the symbol ⋯⋯ are as defined hereinbefore,
which is condensed with a cyanide salt to obtain a compound of formula (VIII):

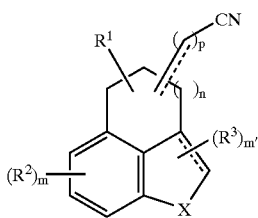

(VIII)

wherein $R^1$, $R^2$, $R^3$, n, p, X m, m' and the symbols ....... are as defined hereinbefore,
which is hydrolysed in an acidic or basic medium to yield a compound of formula (IX):

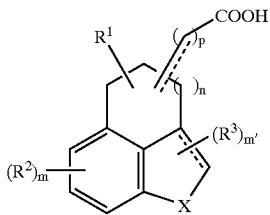

(IX)

wherein $R^1$, $R^2$, $R^3$, n, p, X, m, m' and the symbol ....... are as defined hereinbefore,
which is subjected, after activation to the acid chloride or in the presence of a coupling agent, to the action of an amine $HNR^6R^7$ to yield a compound of formula (I/i), which is a particular case of the compounds of formula (I):

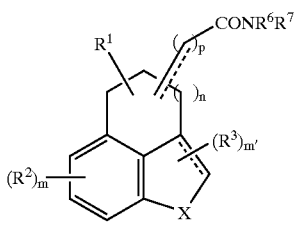

(I/i)

wherein $R^1$, $R^2$, $R^3$, $R^6$, $R^7$, n, p, X, m, m' and the symbol ....... are as defined hereinbefore,
which may be subjected to the action of a thionisation agent, such as Lawesson's reagent, to obtain a compound (I/j), which is a particular case of the compounds of formula (I):

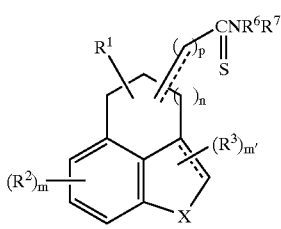

(I/j)

wherein $R^1$, $R^2$, $R^3$, $R^6$, $R^7$, n, p, X, m, m' and the symbol ....... are as defined hereinbefore,
or subjected to the action of a compound of formula (X):

$$Z=C=NR^6R^7 \quad (X)$$

wherein Z, $R^6$ and $R^7$ are as defined hereinbefore, to yield a compound of formula (I/k), which is a particular case of the compounds of formula (I):

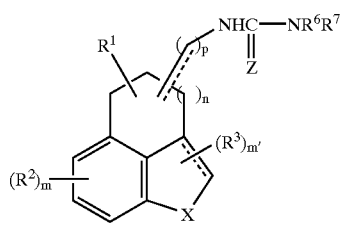

(I/k)

wherein $R^1$, $R^2$, $R^3$, $R^6$, $R^7$, n, p, Z, m, m' and the symbol ....... are as defined hereinbefore, which may be condensed with a compound of formula (V) to yield a compound of formula (I/l), which is a particular case of the compounds of formula (I):

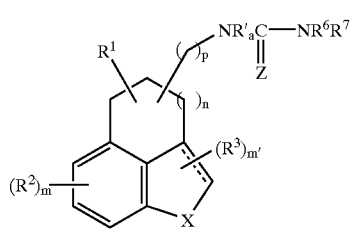

(I/l)

wherein $R^1$, $R^2$, $R^3$, $R^6$, $R^7$, $R'_a$, n, p, X, Z, m, m' and the symbol ....... are as defined hereinbefore,
which compounds (I/a) to (I/l) can be purified according to a conventional separation technique, are converted, if desired, into their addition salts with a pharmaceutically acceptable acid or base, and separated, where appropriate, into their isomers according to a conventional separation technique.

The invention relates also to a process for the preparation of compounds of formula (I) wherein A forms with the groups to which it is bonded a tricyclic system of formula ($A_2$), ($A_3$) or ($A_4$), which process is characterised in that there is used as starting material:

a compound of formula (XI):

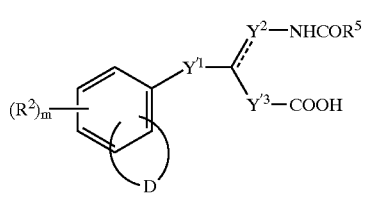

(XI)

wherein $R^2$, $R^5$, $Y^2$, m and the symbol ....... are as defined hereinbefore, and
$Y'^1$ represents a $(CH_2)_{q'}$ group substituted by an $R^1$ group wherein q' and $R^1$ are as defined hereinbefore,
$Y'^3$ represents a $(CH_2)_{q''}$ group substituted by an $R^1$ group wherein q" and $R^1$ are as defined hereinbefore,
where $0 \leq (q'+q'') \leq 4$ and $R^1$ must represent a hydrogen atom in at least one of the two groups $Y'^1$ and $Y'^3$,
and D forms, with the benzene ring, one of the three structures ($A_{2a}$), ($A_{3a}$) and ($A_{4a}$):

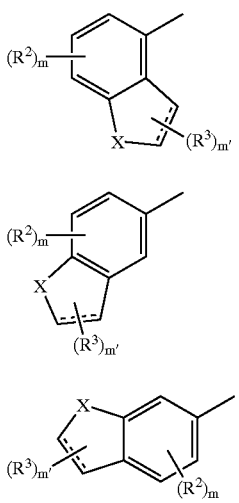

wherein X, R², R³, m, m' and the symbol ⁓ are as defined hereinbefore, which is successively cyclised reacted with a Lewis acid to obtain a compound of formula (I/m), which is a particular case of the compounds of formula (I):

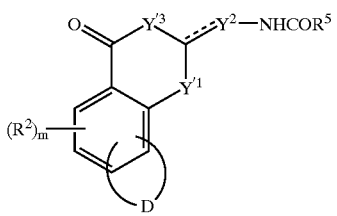

wherein R², R⁵, D, $Y'^1$, $Y^2$, $Y'^3$, m and the symbol ⁓ are as defined hereinbefore, which may be reduced to yield a compound of formula (I/n), which is a particular case of the compounds of formula (I):

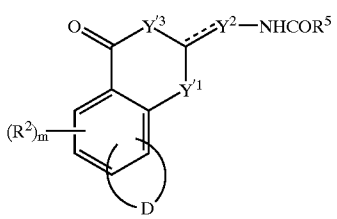

wherein R², R⁵, D, $Y'^1$, $Y'^2$, $Y'^3$, m and the symbol ⁓ are as defined hereinbefore, or a compound of formula (XII):

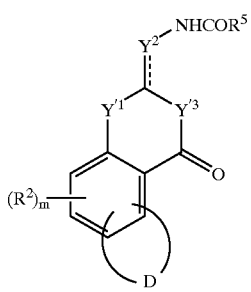

wherein R², R⁵, D, $Y'^1$, $Y^2$, $Y'^3$, m and the symbol ⁓ are as defined hereinbefore, which is successively cyclised reacted with a Lewis acid to yield a compound of formula (I/o), which is a particular case of the compounds of formula (I):

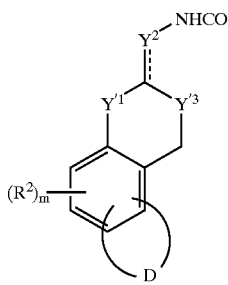

wherein R², R⁵, D, $Y'^1$, $Y^2$, $Y'^3$, m and the symbol ⁓ are as defined hereinbefore, which may be reduced to yield a compound of formula (I/p), which is a particular case of the compounds of formula (I):

(I/p)

wherein R², R⁵, D, $Y'^1$, $Y^2$, $Y'^3$, m and the symbol ⁓ are as defined hereinbefore, the totality of the compounds (I/m), (I/n), (I/o) and (I/p) constituting the compounds (I/q), a particular case of the compounds of formula (I):

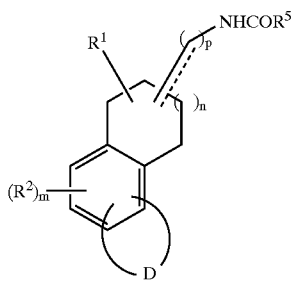

(I/q)

wherein $R^1$, $R^2$, $R^5$, D, n, p, m and the symbol ....... are as defined hereinbefore, which is either:

subjected to the action of a compound of formula (V) to yield a compound of formula (I/r), which is a particular case of the compounds of formula (I):

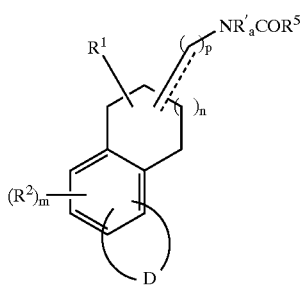

(I/r)

wherein $R^1$, $R^2$, $R^5$, $R'_a$, D, n, p, m and the symbol ....... are as defined hereinbefore, the totality of the compounds (I/q) and (I/r) constituting the compounds (I/s), a particular case of the compounds of formula (I):

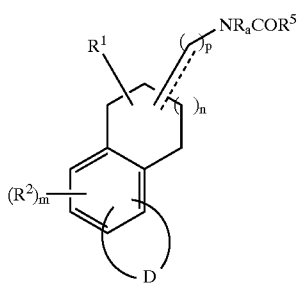

(I/s)

wherein $R^1$, $R^2$, $R^5$, $R_a$, D, n, p, m and the symbol ....... are as defined hereinbefore, which may be subjected to the action of a thionisation agent, such as Lawesson's reagent, to obtain a compound of formula (I/t), which is a particular case of the compounds of formula (I):

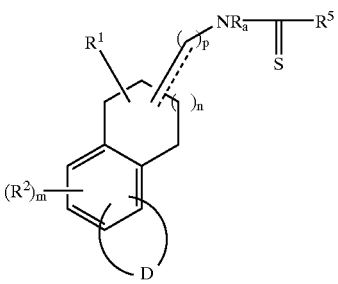

(I/t)

or hydrolysed in a basic medium to yield a compound of formula (XIII):

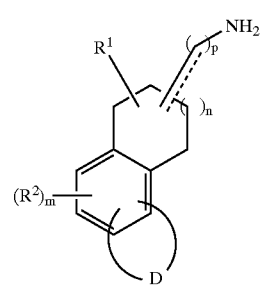

(XIII)

wherein $R^1$, $R^2$, D, n, p, m and the symbol ....... are as defined hereinbefore, which is either:

subjected successively (as for the synthesis of the compound of formula (I/i) starting from a compound of formula (VI))
to the action of a pyrylium salt
to the action of a cyanide salt
to acidic or basic hydrolysis
to condensation, after activation or in the presence of a coupling agent, with an amine $HNR^6R^7$ to yield a compound of formula (I/u), which is a particular case of the compounds of formula (I):

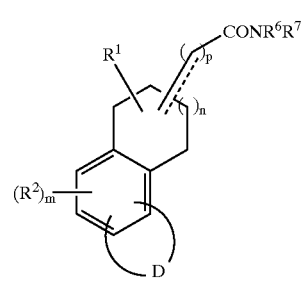

(I/u)

wherein $R^1$, $R^2$, $R^6$, $R^7$, D, n, p, m and the symbol ....... are as defined hereinbefore, which may be subjected to the action of a thionisation agent, such as Lawesson's reagent, to obtain a compound of formula (I/v), which is a particular case of the compounds of formula (I):

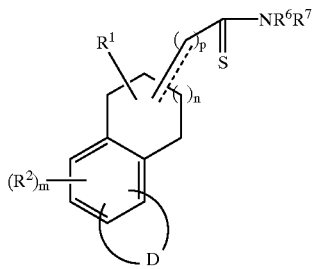

wherein $R^1$, $R^2$, $R^6$, $R^7$, D, n, p, m and the symbol ...... are as defined hereinbefore, or subjected to the action of a compound of formula (X) to yield a compound of formula (I/w), which is a particular case of the compounds of formula (I):

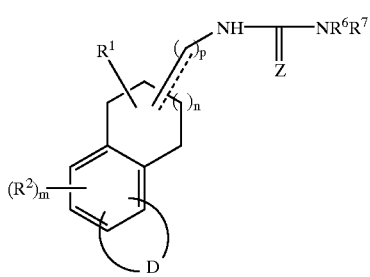

wherein $R^1$, $R^2$, $R^6$, $R^7$, D, Z, n, p, m and the symbol ...... are as defined hereinbefore,
which may be condensed with a compound of formula (V) to yield a compound of formula (I/x), which is a particular case of the compounds of formula (I):

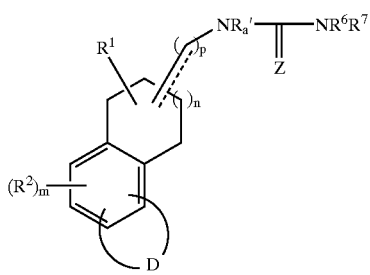

wherein $R^1$, $R^2$, $R^6$, $R^7$, $R'_a$, D, Z, n, p, m and the symbol ...... are as defined hereinbefore,
which compounds (I/m) to (I/x) can be purified according to a conventional separation technique, are converted, if desired, into their addition salts with a pharmaceutically acceptable acid or base, and separated, where appropriate, into their isomers according to a conventional separation technique.

Moreover, the compounds of formulae (I/a) to (I/l), which are particular cases of the compounds of formula (I) substituted by the

chain in the a or c position can be obtained by a preparation process which is characterised in that there is used as starting material a compound of formula (XIV):

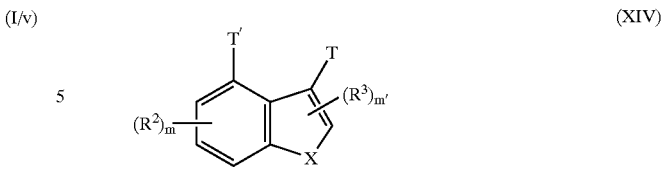

wherein $R^2$, $R^3$, X, m and m' are as defined hereinbefore and T and T', which are different, represent a hydrogen atom or a —CHO group, which is subjected to a Wittig reaction and then to catalytic reduction to obtain a compound of formula (XV):

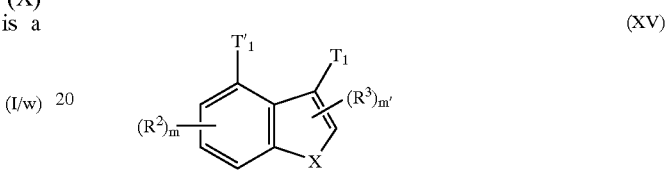

wherein $R^2$, $R^3$, X, m and m' are as defined hereinbefore and $T'_1$ and $T_1$ represent a hydrogen atom or a group of formula (XVI):

wherein G represents a $(CH_2)_{n'}$ group wherein n'=1, 2 or 3 optionally substituted by an $R^1$ group as defined hereinbefore, with the proviso that one of the two groups $T'_1$ and $T_1$ represents a hydrogen atom, which is successively hydrolysed in a basic medium and then decarboxylated by heating to yield a compound of formula (XVII):

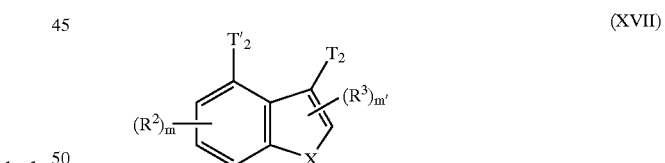

wherein $R^2$, $R^3$, X, m and m' are as defined hereinbefore and $T'_2$ and $T_2$ represent a hydrogen atom or a group of formula (XVIII):

wherein G is as defined hereinbefore, with the proviso that one of the two groups $T'_2$ and $T_2$ represents a hydrogen atom, which is subjected to cyclisation in the presence of a Lewis acid after activation to the oxalyl chloride, to yield a compound of formula (XIX):

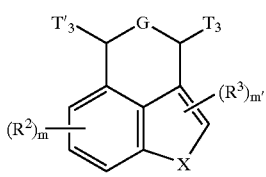
(XIX)

wherein $R^2$, $R^3$, X, G, m and m' are as defined hereinbefore, and $T'_3$ and $T_3$, which are different, represent a hydrogen atom or an oxo group, which is subjected either:

to a Wittig reaction (optionally followed by reduction) and then to hydrolysis to yield a compound of formula (XX):

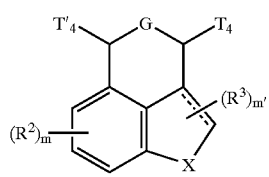
(XX)

wherein $R^2$, $R^3$, X, G, m, m' and the symbol ⋯⋯ are as defined hereinbefore, and each of $T_4$ and $T'_4$ represents a hydrogen atom or forms, with the carbon atom carrying it,

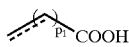

group wherein $p_1$ is 1, 2 or 3, with the proviso that one of the two groups $T_4$ and $T'_4$ represents a hydrogen atom, or successively
  to reduction to the corresponding alcohol
  to halogenation in the presence of $SOCl_2$ for example
  to condensation with a cyanide salt
  to acidic or basic hydrolysis
to yield a compound of formula (XXI):

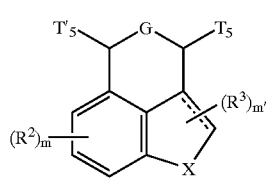
(XXI)

wherein $R^2$, $R^3$, X, G, m, m' and the symbol ⋯⋯ are as defined hereinbefore, and $T'_5$ and $T_5$, which are different, represent a hydrogen atom or a COOH group, the totality of the compounds (XX) and (XXI) constituting the compounds of formula (XXII):

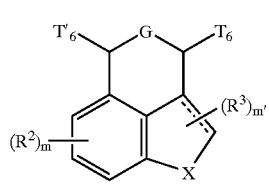
(XXII)

wherein $R_2$, $R_3$, X, G, m, m' and the symbol ⋯⋯ are as defined hereinbefore, and each of $T'_6$ and $T_6$ represents a hydrogen atom or forms, with the carbon atom carrying it,

group wherein p is as defined hereinbefore,
with the proviso that one of the two groups $T'_6$ and $T_6$ represents a hydrogen atom,
which compound (XXII) can also be obtained starting from a compound of formula (XIX) by condensation according to a Wittig reaction with a compound containing a nitrile group (followed by optional reduction of the double bond), and hydrolysis of the nitrile, which compound (XXII) is either:

subjected, after activation to the acid chloride or in the presence of a coupling agent, to the action of an amine $HNR^6R^7$ to yield a compound of formula (I/y), which is a particular case of the compounds of formula (I):

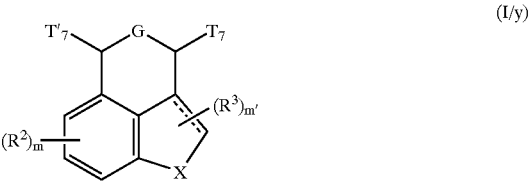
(I/y)

wherein $R^2$, $R^3$, X, G, m, m' and the symbol ⋯⋯ are as defined hereinbefore, and each of $T'_7$ and $T_7$ represents a hydrogen atom or forms, with the carbon atom carrying it,

group wherein p, $R^6$ and $R^7$ are as defined hereinbefore,
with the proviso that one of the two groups $T'_7$ and $T_7$ represents a hydrogen atom,
which may be subjected to the action of a thionisation agent, such as Lawesson's reagent, to obtain a compound (I/z), which is a particular case of the compounds of formula (I):

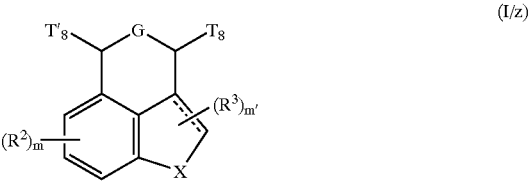
(I/z)

wherein $R^2$, $R^3$, X, G, m, m' and the symbol ⋯⋯ are as defined hereinbefore, and each of $T'_8$ and $T_8$ represents a hydrogen atom or forms, with the carbon atom carrying it,

group wherein p, $R^6$ and $R^7$ are as defined hereinbefore,
with the proviso that one of the two groups $T_8$ and $T'_8$ represents a hydrogen atom, or activated to the acid chloride, and then treated with an azide, heated to the corresponding isocyanate and then hydrolysed to yield a compound of formula (XXIII):

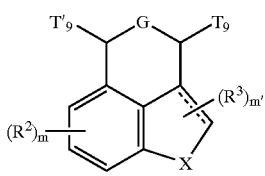

(XXIII)

wherein $R^2$, $R^3$, X, G, m, m' and the symbol ...... are as defined hereinbefore, and each of $T'_9$ and $T_9$ represents a hydrogen atom or forms, with the carbon atom carrying it,

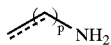

group wherein p is as defined hereinbefore,
with the proviso that one of the two groups $T_9$ and $T'_9$ represents a hydrogen atom,
which compound of formula (XXIII) can also be obtained starting from a compound of formula (XIX) by condensation according to a Wittig reaction with a compound containing a nitrile group followed by reduction of the nitrile,
which compound of formula (XXIII) is condensed with:
   an acyl chloride $ClCOR^5$ or the corresponding acid anhydride (mixed or symmetrical) wherein $R^5$ is as defined hereinbefore, to yield a compound of formula (I/aa), which is a particular case of the compounds of formula (I):

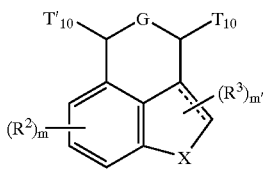

(I/aa)

wherein $R^2$, $R^3$, X, G, m, m' and the symbol ...... are as defined hereinbefore, and each of $T'_{10}$ and $T_{10}$ represents a hydrogen atom or forms, with the carbon atom carrying it,

group wherein p and $R^5$ are as defined hereinbefore,
with the proviso that one of the two groups $T'_{10}$ and $T_{10}$ represents a hydrogen atom,
which may be subjected to the action of a thionisation agent, such as Lawesson's reagent, and/or substituted after the action of a compound of formula (V) to yield a compound of formula (I/ab), which is a particular case of the compounds of formula (I):

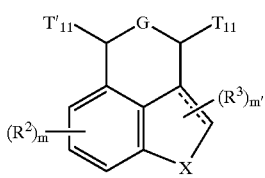

(I/ab)

wherein $R^2$, $R^3$, X, G, m, m' and the symbol ...... are as defined hereinbefore, and each of $T'_{11}$ and $T_{11}$ represents a hydrogen atom or forms, with the carbon atom carrying it,

group wherein p, $R_a$, $R^5$ and Z are as defined hereinbefore, with the proviso that one of the two groups $T'_{11}$ and $T_{11}$ represents a hydrogen atom,
which compounds (I/y) to (I/ab) can be purified according to a conventional separation technique, are converted, if desired, into their addition salts with a pharmaceutically acceptable acid or base, and separated, where appropriate, into their isomers according to a conventional separation technique.

The compounds (I/m) to (I/v) can also be obtained according to a similar process which is characterised in that there is used as starting material a compound of formula (XXIV):

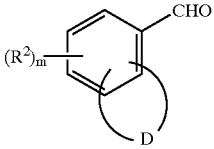

(XXIV)

wherein $R_2$, D and m are as defined hereinbefore.
The starting materials are:
   commercially available,
   readily available to the person skilled in the art by using conventional chemical reactions, or
   described in the literature, such as, for example, in Application EP 737 670.

The compounds of the invention and the pharmaceutical compositions containing them have proved to be useful in the treatment of disorders of the melatoninergic system. The pharmacological study of the compounds of the invention has in fact shown them to be atoxic, to have very high selective affinity for melatonin receptors and to have significant activities in respect of the central nervous system and, in particular, therapeutic properties in respect of sleep disorders, anxiolytic, antipsychotic and analgesic properties and properties in respect of microcirculation have been found, enabling it to be established that the compounds of the invention are useful in the treatment of stress, sleep disorders, anxiety, seasonal affective disorders, cardiovascular pathologies, insomnia and fatigue due to jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss and Alzheimer's disease, and in cerebral circulation disorders. In another field of activity, the compounds of the invention appear, in treatment, to have ovulation-inhibiting and immunomodulating properties and they appear to be able to be used in the treatment of cancers.

The compounds will preferably be used in the treatment of seasonal affective disorders, sleep disorders, cardiovascular pathologies, insomnia and fatigue due to jetlag, appetite disorders and obesity. For example, the compounds will be used in the treatment of seasonal affective disorders and sleep disorders.

The present invention relates also to pharmaceutical compositions comprising at least one compound of formula (I) on its own or in combination with one or more pharmaceutically acceptable excipients.

Amongst the pharmaceutical compositions according to the invention there may be mentioned more especially those that are suitable for oral, parenteral, nasal, per- or transcutaneous, rectal, perlingual, ocular or respiratory administration and especially tablets or dragees, sublingual tablets, sachets, paquets, gelatin capsules, glossettes, lozenges, suppositories, creams, ointments, dermal gels, and drinkable or injectable ampoules.

The dosage varies according to the sex, age and weight of the patient, the route of administration, the nature of the therapeutic indication, or of any associated treatments and ranges from 0.01 mg to 1 g per 24 hours in 1 or more administrations.

The following Examples illustrate the invention but do not limit it in any way. The following Preparations yield synthesis intermediates for use in the preparation of the compounds of the invention.

PREPARATION 1

(4-Methoxy-2,3-dihydro-1H-1-phenalenyl)methylamine

Step A: Diethyl 2-[(2-methoxy-1-naphthyl)methylene]malonate

2-Methoxy-1-naphthaldehyde (25 g, $1.34.10^{-1}$ mol) in benzene (200 ml) is heated for 20 hours at reflux in the presence of diethyl malonate (25 ml, $1.65.10^{-1}$ mol, 1.23 eq.) and piperidine (2 ml, $2.02.10^{-2}$ mol, 0.15 eq.) in a Dean-Stark apparatus. After adding a few additional drops of piperidine, the mixture is returned to reflux for 20 hours. The reaction mixture is diluted with toluene (200 ml) and washed with water (125 ml). After separation of the phases, the organic phase is treated with a 1N hydrochloric acid solution (190 ml), then with a saturated $NaHCO_3$ solution (125 ml) and with a saturated NaCl solution (125 ml). After drying over $MgSO_4$ and evaporation under reduced pressure, the oil obtained is recrystallised from cyclohexane.

Melting point: 86° C.; Elemental microanalysis:

|  | C | H |
| --- | --- | --- |
| % calculated | 69.50 | 6.14 |
| % found | 69.53 | 6.23 |

Step B: Diethyl 2-[(2-methoxy-1-naphthyl)methyl]malonate

After being solubilised in ethanol (510 ml), the unsaturated compound obtained in Step A (10 g, $3.05.10^{-2}$ mol) is hydrogenated in the presence of Raney nickel at ambient temperature with vigorous stirring. The reaction is monitored by TLC and GPC after 4 hours' hydrogenation. After it has been established that the starting material has disappeared, the catalyst is filtered off over Celite and the ethanol is evaporated off under reduced pressure. The title product is obtained in the form of a colourless oil.

Elemental microanalysis:

|  | C | H |
| --- | --- | --- |
| % calculated | 69.07 | 6.71 |
| % found | 69.14 | 6.76 |

Step C: 2-[(2-Methoxy-1-naphthyl)methyl]malonic Acid

In a 1 litre single-necked flask, the compound obtained in Step B (20 g, $6.05.10^{-2}$ mol) is heated at reflux in the presence of sodium hydroxide (20 g, $5.00.10^{-1}$ mol) and water (340 ml) for 4 hours 30 minutes. After cooling, the mixture is diluted with 150 ml of water, filtered through filter paper and acidified using concentrated hydrochloric acid in the hot state (80–90° C.); the white microspheres formed in the hot state are filtered off over a frit after complete cooling. The diacid is washed with cold water. After drying in an oven (110° C.) for one night, the title compound is dried in a desiccator in the presence of $P_2O_5$.

Melting point: 174–175° C.; Elemental microanalysis:

|  | C | H |
| --- | --- | --- |
| % calculated | 65.69 | 5.15 |
| % found | 65.64 | 5.18 |

Step D: 3-(2-Methoxy-1-naphthyl)propanoic Acid

Decarboxylation of the diacid obtained in Step C (8.1 g, $2.95.10^{-2}$ mol) is carried out in a 100 ml single-necked flask purged with argon and heated by a metal bath at 165–178° C. until the evolution of gas has ceased. The acid is recrystallised from a $CH_2Cl_2$/petroleum ether mixture.

Melting point: 131° C.

Step E: 4-Methoxy-2,3-dihydro-1H-phenalenone

In a 250 ml three-necked flask, oxalyl chloride (1.95 ml, $2.19.10^{-2}$ mol, 1 eq.) is added dropwise, under argon, to a solution of the acid obtained in Step D (5 g, $2.17.10^{-2}$ mol) in anhydrous dichloromethane (225 ml) at 0° C. A few drops of anhydrous dimethylformamide are then added. After 1 hour at 0° C., slight evolution of gas is still observed and the three-necked flask is left at ambient temperature for 40 minutes. After return to 0° C., aluminium chloride (7.5 g, $5.62.10^{-2}$ mol, 2.6 eq.) is added using a spatula. The initially yellow solution becomes red, orange and then khaki-green. After 15 minutes' stirring at 0° C., the mixture is poured into an ice/1N HCl mixture. After separation of the phases and washings of the acidic aqueous phase with dichloromethane, the combined organic phases are washed with water, then treated with a saturated $NaHCO_3$ solution and finally washed with a saturated NaCl solution. After drying over $MgSO_4$ and evaporation under reduced pressure, the yellow oil obtained crystallises in a freezer.

Melting point: 65° C.

Step F: Ethyl 2-(4-Methoxy-2,3-dihydro-1H-1-phenalenylidene)acetate

Triethyl phosphonoacetate (3.22 ml, $1.63.10^{-2}$ mol, 1.15 eq) is added dropwise, under argon, to a suspension, in anhydrous THF (24 ml), of 60% sodium hydride in oil (650 mg, $1.63.10^{-2}$ mol, 1.15 eq.), previously washed with pentane. After 50 minutes' stirring at ambient temperature, the compound obtained in Step E (3 g, $1.41.10^{-2}$ mol, 1 eq.), dissolved in anhydrous THF (20 ml), is added over 10 minutes. The reaction mixture is stirred for one night at ambient temperature. The mixture is diluted with water, filtered over Celite and extracted several times with ether. After drying over $MgSO_4$ and evaporation under reduced pressure, the oily residue is chromatographed using $CH_2Cl_2$/petroleum ether 60/40. The orange-yellow oil obtained crystallises at ambient temperature and corresponds to a mixture of the two E/Z isomers, their average ratio of 45/55 being determined by GPC analysis.

Elemental microanalysis: (E/Z mixture);

|  | C | H |
|---|---|---|
| % calculated | 76.57 | 6.43 |
| % found | 76.43 | 6.58 |

Step G: Ethyl2-(4-Methoxy-2,3-dihydro-1H-1-phenalenyl)acetate 55 mg of $PdCl_2$ in 5 ml of methanol are treated with 25 mg of sodium borohydride. After 15 minutes' stirring, the compound obtained in Step F (1 g, $3.54.10^{-3}$ mol), diluted with methanol (15 ml), is added. The mixture is purged with argon and placed under hydrogen. The reaction is monitored by GPC analysis. After 1 hour 30 minutes' hydrogenation, the reaction mixture is filtered over Celite, rinsed and then evaporated under reduced pressure.

Step H: 2-(4-Methoxy-2,3-dihydro-1H-1-phenalenyl) acetic Acid

The ester obtained in Step G (2 g, $7.03.10^{-3}$ mol) is heated at reflux in the presence of potassium hydroxide (4 g, $7.13.10^{-2}$ mol, 10 eq.), water (16 ml) and methanol (16 ml) for one night. After evaporating off the solvent, the residue is taken up in water and extracted twice with ether. The basic aqueous phase is acidified using concentrated HCl in the cold state. The acid is extracted with ethyl acetate and dried over $MgSO_4$. After evaporating off the solvent under reduced pressure, a brown oil which crystallises at ambient temperature is obtained.

Melting point: 120.5° C.; Elemental microanalysis:

|  | C | H |
|---|---|---|
| % calculated | 74.98 | 6.29 |
| % found | 74.80 | 6.34 |

Step, I: (4-Methoxy-2,3-dihydro-1H-1-phenalenyl)methylamine Hydrochloride

In a 100 ml three-necked flask, triethylamine (645 μl, 4.63 mmol. 1.15 eq.) is added dropwise to a solution, cooled to 0° C., of the acid obtained in Step H (1.03 g, 4.02 mmol) in a mixture of acetone (17 ml) and water (1 ml). Ethyl chloroformate (500 μl, 5.23 mmol, 1.30 eq.) is then slowly added at 0° C.; evolution of gas is visible. The mixture is stirred at 0° C. for 30 minutes; after it has been established, on TLC ($CH_2Cl_2$), that the starting material has disappeared, a solution of sodium azide (350 mg, 5.23 mmol, 1.30 eq.) in water (1.7 ml) is added at 0° C. The mixture is maintained at that temperature for one hour. TLC ($CH_2Cl_2$) indicates the formation of the azide. The mixture is poured into an ice/water mixture and is then extracted with ether. The ethereal phases are washed with water, then dried over $Na_2SO_4$ and evaporated in vacuo without heating. After being taken up in 10 ml of anhydrous toluene, the azide is heated at 80° C. until nitrogen is no longer evolved. After evaporating off the toluene, the oil corresponding to the isocyanate is heated at 100° C. together with a 20% hydrochloric acid solution (8 ml) for 3 hours; the mixture is stirred for one night at ambient temperature. The reaction mixture is diluted with water, filtered through filter paper and extracted with ether. The aqueous phase of pH=1 is rendered basic using solid sodium carbonate and then extracted with ether. The combined ethereal phases are washed with water and dried over $K_2CO_3$. After evaporating off the solvent under reduced pressure, the amine is converted into the hydrochloride after being solubilised in ether and treated with a 4N ethereal hydrogen chloride solution.

Melting point: 237° C.; Elemental microanalysis:

|  | C | H | N |
|---|---|---|---|
| % calculated | 68.30 | 6.88 | 5.31 |
| % found | 68.23 | 6.90 | 5.25 |

By proceeding as for Preparation 1, starting from the appropriately substituted aldehyde, Preparations 2 to 18 are obtained.

PREPARATION 2
2,3-Dihydro-1H-1-phenalenylmethylamine

PREPARATION 3
(4,9-Dimethoxy-2,3-dihydro-1H-1-phenalenyl)methylamine

PREPARATION 4
(4-Ethyl-2,3-dihydro-1H-1-phenalenyl)methylamine

PREPARATION 5
(4-Chloro-2,3-dihydro-1H-1-phenalenyl)methylamine

PREPARATION 6
(6-Methoxy-4,5-dihydro-3H-benzo[cd]isobenzofuran-5-yl)-methylamine PREPARATION 7
(6-Methoxy-4,5-dihydro-3H-benzo[cd]isobenzofuran-3-yl)-methylamine PREPARATION 8
(6-Ethyl-4,5-dihydro-3H-benzo[cd]isobenzofuran-5-yl)methylamine PREPARATION 9
(6-Ethyl-4,5-dihydro-3H-benzo[cd]isobenzofuran-3-yl)methylamine PREPARATION 10
(6-Methoxy-4,5-dihydro-3H-naphtho[1,8-bc]thiophen-5-yl)-methylamine PREPARATION 11
(6-Methoxy-4,5-dihydro-3H-naphtho[1,8-bc]thiophen-3-yl)-methylamine PREPARATION 12
(6-Methoxy-1,3,4,5-tetrahydrobenzo[cd]indol-3-yl)methylamine PREPARATION 13
(6-Methoxy-1,3,4,5-tetrahydro-3-acenaphthylenyl)methylamine PREPARATION 14
(7-Methoxy-2,3-dihydro-1H-cyclopenta[b]naphthalen-1-yl)-methylamine PREPARATION 15
(6,7-Dihydro-5H-indeno[5,6-b]thiophen-5-yl)methylamine PREPARATION 16
(7,8-Dihydro-6H-indeno[4,5-b]thiophen-6-yl)methylamine PREPARATION 17
(7,8-Dihydro-6H-indeno[4,5-b]thiophen-8-yl)methylamine PREPARATION 18
(7,8-Dihydro-6H-indeno[5,4-b]thiophen-8-yl)methylamine PREPARATION 19
2-(4-Methoxy-2,3-dihydro-1H-1-phenalenyl)ethylamine

Step A: 2-(4-Methoxy-2,3-dihydro-1H-1-phenalenylidene)acetonitrile

Diethyl cyanomethylphosphonate (1.75 ml, $1.08 \cdot 10^{-2}$ mol. 1.15 eq) is added dropwise, under argon, to a suspension, in anhydrous THF (15 ml), of 60% sodium hydride in oil (433 mg, $1.08 \cdot 10^{-2}$ mol, 1.15 eq.), previously washed with pentane. After 50 minutes' stirring at ambient temperature, the compound obtained in Step E of Preparation 1 (2 g, $9.42 \cdot 10^{-2}$ mol, 1 eq.), dissolved in anhydrous THF (15 ml), is added over 10 minutes. The reaction mixture is stirred for one night at ambient temperature. The mixture is diluted with water, filtered over Celite and extracted several times with ether. After drying over $MgSO_4$ and evaporating under reduced pressure, the oily residue is chromatographed using $CH_2Cl_2$/petroleum ether 60/40. The orange-yellow oil obtained crystallises at ambient temperature and corresponds to a mixture of the two E/Z isomers in a variable ratio of from 60/40 to 40/60.

Elemental microanalysis:

|  | C | H | N |
| --- | --- | --- | --- |
| % calculated | 81.68 | 5.57 | 5.95 |
| % found | 81.62 | 5.65 | 5.86 |

Step B: 2-(4-Methoxy-2,3-dihydro-1H-1-phenalenyl) acetonitrile

The catalyst is prepared starting from 55 mg of $PdCl_2$ in 5 ml of methanol treated with 25 mg of sodium borohydride. After 15 minutes' stirring, the compound obtained in Step A (1 g, $4.25 \cdot 10^{-3}$ mol), diluted with methanol (15 ml), is incorporated. The mixture is purged with argon and placed under hydrogen. The reaction is monitored by GPC analysis. After 2 hours 30 minutes' hydrogenation, the reaction mixture is filtered over Celite, rinsed and then evaporated under reduced pressure. The title product is isolated in the form of a colourless oil.

Elemental microanalysis:

|  | C | H | N |
| --- | --- | --- | --- |
| % calculated | 80.98 | 6.37 | 5.90 |
| % found | 80.96 | 6.47 | 5.91 |

Step C: 2-(4-Methoxy-2,3-dihydro-1H-1-phenalenyl) ethylamine Hydrochloride

The nitrile obtained in Step B (1.26 g, $5.31 \cdot 10^{-3}$ mol), diluted with methanol (15 ml), is hydrogenated at ambient temperature, with vigorous stirring, in the presence of ammonium hydroxide (1 ml) and Raney nickel. 48 hours are necessary for the starting material to disappear. After filtering over Celite, then rinsing and evaporating off the solvent under reduced pressure, the amine is taken up in ether and treated with a few drops of 4N ethereal hydrogen chloride. The hydrochloride is recrystallised from an ethanol/ether mixture.

Melting point: 223° C.; Elemental microanalysis:

|  | C | H | N |
| --- | --- | --- | --- |
| % calculated | 80.98 | 6.37 | 5.90 |
| % found | 80.96 | 6.47 | 5.91 |

By proceeding as for Preparation 19, starting from the corresponding ketonic intermediate, Preparations 20 to 26 are obtained:

PREPARATION 20

2-(6-Methoxy-4,5-dihydro-3H-benzo[cd] isobenzofuran-5-yl)-ethylamine

PREPARATION 21

2-(6-Chloro-4,5-dihydro-3H-benzo[cd] isobenzofuran-5-yl)ethyl-amine

PREPARATION 22

2-(6-Methoxy-4,5-dihydro-3H-benzo[cd] isobenzofuran-3-yl)-ethylamine

PREPARATION 23

2-(6-Ethyl-4,5-dihydro-3H-naphtho[1,8-bc]thiophen-3-yl)ethylamine

PREPARATION 24

2-(6-Methoxy-1,3,4,5-tetrahydro-3-acenaphthylenyl) ethylamine

PREPARATION 25

2-(6-Methoxy-1,3,4,5-tetrahydrobenzo[Cd]indol-3-yl)ethylamine

PREPARATION 26

2-(1,3,4,5-Tetrahydrobenzo[cd]indol-3-yl) ethylamine

PREPARATION 27

2-(4-Methoxy-2,3-dihydro-1H-phenalenyl)acetic Acid

A mixture of the compound obtained in Step B of Preparation 19 and a 10% sodium hydroxide solution is heated at reflux. The reaction is monitored by TLC. When the starting material has disappeared, the reaction mixture is cooled and extracted at a basic pH; the mixture is then acidified using 2N, and then 3N, hydrochloric acid and extracted again. After evaporating off the solvents under reduced pressure, the title acid is obtained in the pure form.

By proceeding as for Preparation 27, starting from the corresponding nitrile, Preparations 28 to 31 are obtained:

PREPARATION 28

2-(4-Chloro-2,3-dihydro-1H-1-phenalenyl)acetic Acid

PREPARATION 29

2-(6-Chloro-4,5-dihydro-3H-benzo[cd] isobenzofuran-5-yl)acetic Acid

PREPARATION 30

2-(6-Methoxy-1,3,4,5-tetrahydrobenzo[cd]indol-3-yl)acetic Acid

PREPARATION 31

2-(6-Methoxy-1,3,4,5-tetrahydro-3-acenaphthylenyl) acetic Acid

PREPARATION 32

3-(4-Methoxy-2,3-dihydro-1H-1-phenalenyl) propylamine

Step A: Ethyl3-(4-methoxy-2,3-dihydro-1H-1-phenalenylidene)propanoate

The procedure is as in Step F of Preparation 1, with replacement of the triethyl phosphonoacetate with triethyl phosphonopropanoate.

Steps B, C and D are identical to Steps G, H and I of Preparation 1.

Preparation 33 is obtained by proceeding as for Preparation 32, starting from the ketone obtained in Preparation 3.

PREPARATION 33

3-(4,9-Dimethoxy-2,3-dihydro-1H-1-phenalenyl) propylamine

PREPARATION 34

4-(4-Methoxy-2,3-dihydro-1H-1-phenalenyl) butanoic Acid

Step A: 4-(4-Methoxy-2,3-dihydro-1H-1-phenalenyl) nitrobutane

The ketone obtained in Step E of Preparation 1 is subjected to the conditions of Steps A and B of Preparation 19, with replacement of the diethyl cyanomethylphosphonate with diethyl cyanopropylphosphonate.

Step B: 4-(4-Methoxy-2,3-dihydro-1H-1-phenalenyl) butanoic Acid

Hydrolysis of the nitrile obtained in Step A is carried out under the conditions of Preparation 27.

PREPARATION 35

2-(2,2a,3,4-Tetrahydroindeno[7,1-bc]furan-4-yl) ethylamine

The procedure is as in Preparation 19, starting from 2,3-dihydrobenzo[b]furan-3-one.

PREPARATION 36

2-(2,2a,3,4-Tetrahydroindeno[7,1-bc]thiophen-4-yl) ethylamine

The title compound is obtained by following the procedure of Preparation 35, starting from 2,3-dihydrobenzo[b] thiophen-3-one.

PREPARATION 37

2-(1,6-Dimethoxy-7,8,9,10-tetrahydrocycloheptaidelnaphthalen-7-yl)ethylamine

Step A: Ethyl4-(2,7-dimethoxy-1-naphthyl)-3-butenoate

The procedure is as in Step F of Preparation 1, ethyl triethylphosphonopropanoate being condensed with 2,7-dimethoxy-1-naphthaldehyde.

Step B: Ethyl4-(2,7-dimethoxy-1-naphthyl)butanoate

Reduction of the compound obtained in Step A is carried out under the conditions of Step G of Preparation 1.

Step C: 4-(2,7-Dimethoxy-1-naphthyl)butanoic Acid

Hydrolysis of the ester obtained in Step B is carried out under the conditions of Step H of Preparation 1.

Step D: 2-(1,6-Dimethoxy-7,8,9,10-tetrahydrocyclohepta[de]naphthalen-7-yl)-ethylamine The procedure is as in Step E of Preparation 1 and Steps A, B and C of Preparation 19.

PREPARATION 38

2-(1-Methoxy-7,8,9,10-tetrahydrocyclohepta[de] naphthalen-7-yl)-methylamine

Step A: 4-(2-Methoxy-1-naphthyl)butanoic Acid

The procedure is as in Steps A, B and C of Preparation 37, starting from 2-methoxy-1-naphthaldehyde.

Step B: 2-(1-Methoxy-7,8,9,10-tetrahydrocyclohepta[de] naphthalen-7-yl)-methylamine The procedure is as in Steps E, F, G, H and I of Preparation 1.

PREPARATION 39

6,7,8,9-Tetrahydro-2-thiabenzo[cd]azulen-9-yl-methylamine

The procedure is as in Preparation 38, starting from benzo[b]thiophene-4-carbaldehyde.

PREPARATION 40

(5-Methoxy-6,7,8,9-tetrahydro-2-oxobenzo[cd] azulen-9-yl)-methylamine

The procedure is as in Preparation 38, starting from 5-methoxybenzo[b]furan-4-carbaldehyde.

By proceeding as for Preparation 38, starting from the appropriately substituted aldehyde, Preparations 41 to 49 are obtained:

PREPARATION 41

(7-Methoxy-1,2,3,4-tetrahydro-1-anthracenyl) methylamine

PREPARATION 42

(6-Methoxy-1,2,3,4-tetrahydro-1-anthracenyl) methylamine

PREPARATION 43

(5,6,7,8-Tetrahydronaphtho[2,3-b]thiophen-5-yl) methylamine

PREPARATION 44

(3-Ethyl-5,6,7,8-tetrahydronaphtho[2,3-b]thiophen-5-yl)methyl-amine

PREPARATION 45

(6,7,8,9-Tetrahydronaphtho[1,2-b]thiophen-6-yl) methylamine

PREPARATION 46

(6,7,8,9-Tetrahydronaphtho[1,2-b]thiophen-9-yl) methylamine

PREPARATION 47

(6,7,8,9-Tetrahydronaphtho[2,1-b]thiophen-9-yl) methylamine

PREPARATION 48

(1-Methoxy-6,7,8,9-tetrahydronaphtho[2,1-b] thiophen-9-yl)-methylamine

PREPARATION 49

(1-Methoxy-6,7,8,9-tetrahydronaphtho[1,2-b] thiophen-9-yl)-methylamine

PREPARATION 50

(3-Methoxy-2,3-dihydro-1H-1-phenalenyl) methylamine

The procedure is as for Preparation 2, with methanol being added onto the double bond of the diethyl 2-(1-naphthylmethylene)malonate obtained in Step A. Preparations 51 to 61 are obtained according to the methods described in Patent Application EP 737 670.

PREPARATION 51

3-(3,8-Dimethoxy-1,2-dihydro-1-acenaphthylenyl) propylamine

PREPARATION 52

4-(3,8-Dimethoxy-1,2-dihydro-1-acenaphthylenyl) butanoic Acid

PREPARATION 53

(4-Methoxy-2,3-dihydro-1H-2-phenalenyl) methylamine

PREPARATION 54

(4-Ethyl-2,3-dihydro-1H-2-phenalenyl)methylamine

PREPARATION 55

2-(4,9-Dimethoxy-2,3-dihydro-1H-2-phenalenyl) acetic Acid

PREPARATION 56

4-Methoxy-2,3-dihydro-1H-2-phenalenecarboxylic Acid

PREPARATION 57

2-(4-Methoxy-2,3-dihydro-1H-2-phenalenyl) ethylamine

PREPARATION 58

3-(4-Methoxy-2,3-dihydro-1H-2-phenalenyl) propylamine

PREPARATION 59

(6-Chloro-2,3-dihydro-1H-2-phenalenyl) methylamine

PREPARATION 60

(1,6-Dimethoxy-7,8,9,10-tetrahydrocyclohepta[de] naphthalen-8-yl)-methylamine

PREPARATION 61

2-(1,6-Dimethoxy-7,8,9,10-tetrahydrocyclohepta[de] naphthalen-8-yl)acetic Acid

PREPARATION 62

8-Methoxy-1,2-dihydro-1-acenaphthylenylamine

PREPARATION 63

2-(9-Methoxy-2,3-dihydro-1H-1-phenalenyl) acetonitrile

The procedure is as in Steps A and B of Preparation 19.

Melting, point: 116° C.; Elemental microanalysis:

|  | C | H | N |
|---|---|---|---|
| % calculated | 80.98 | 6.37 | 5.90 |
| % found | 80.77 | 6.47 | 5.74 |

PREPARATION 64

2-(4,9-Dimethoxy-2,3-dihydro-1H-1-phenalenyl) ethylamine

The procedure is as in Preparation 19.

PREPARATION 65

(9-Methoxy-2,3-dihydro-1H-1-phenalenyl) methylamine

Step A: 2-(9-Methoxy-2,3-dihydro-1H-1-phenalenyl) acetic Acid

In a 250 ml single-necked flask, the nitrile obtained in Preparation 63 (500 mg, 2.1 $1.10^{-3}$ mol) is heated at reflux in the presence of 30% sodium hydroxide solution (8 ml), methanol (8 ml) and ethanol (8 ml) for 48 hours. After cooling, the mixture is poured into an ice/water mixture. The mixture is acidified using hydrochloric acid and extracted three on times with ethyl acetate and once with dichloromethane. The organic phases are washed separately with water and with a saturated NaCl solution, dried over $MgSO_4$ and then evaporated under reduced pressure. The title acid is obtained in the form of a pale yellow solid.

Melting point: 147° C.; Elemental microanalysis:

|  | C | H |
|---|---|---|
| % calculated + ⅓ $H_2O$ | 73.26 | 6.40 |
| % found | 73.38 | 6.37 |

Step B: (9-Methoxy-2,3-dihydro-1H-1-phenalenyl) methylamine

The title product is obtained starting from the acid of Step A (515 mg, $2.01.10^{-3}$ mol) in a mixture of acetone (20 ml) and water (600 µl), triethylamine (322 µl, $2.31.10^{-3}$ mol, 1.15 eq.) and ethyl chloroformate (250 µl, $2.61.10^{-3}$ mol, 1.30 eq.). The acyl azide is formed by the action of a solution of sodium azide (175 mg, $2.61.10^{-3}$ mol, 1.30 eq.) in water (1 ml). After heating in anhydrous toluene (5 ml), the isocyanate is hydrolysed with a 20% hydrochloric acid solution (6 ml). The mixture is stirred for one night at ambient temperature. The reaction mixture is diluted with water, filtered through filter paper and extracted with ether. The aqueous phase of pH=1 is rendered basic with solid sodium carbonate and then extracted with ether. The combined ethereal phases are washed with water and dried over $K_2CO_3$. After evaporating off the solvent under reduced pressure, the amine is converted into the hydrochloride after being solubilised in ether and treated with a 4N ethereal hydrogen chloride solution. After drying, the title product is obtained in the form of a white solid.

PREPARATION 66

[(E)-2-(4-Methoxy-2,3-dihydro-1H-phenalenyl)] acetic Acid

The trans ester obtained in Step F of Preparation 1 (760 mg, $2.69.10^{-3}$ mol) is heated at reflux in the presence of potassium hydroxide (377 mg, $6.73.10^{-3}$ mol, 2.5 eq.), water (10 ml) and methanol (10 ml) for one night. After evaporating off the solvent, the residue is taken up in water and extracted twice with ether. The basic aqueous phase is acidified using concentrated HCl in the cold state. The acid is extracted with ethyl acetate, washed with water and dried over $MgSO_4$. After evaporating off the solvent under reduced pressure, the title product is obtained in the form of a yellow solid.

Melting point: 208° C.; Elemental microanalysis:

|  | C | H |
|---|---|---|
| % calculated + ⅔ $H_2O$ | 72.17 | 5.80 |
| % found | 72.37 | 5.56 |

PREPARATION 67

[(Z)-2-(4-Methoxy-2,3-dihydro-1H-phenalenyl)] acetic Acid

The procedure is as in Preparation 66, starting from the cis isomer.

Melting point: 187° C.; Elemental microanalysis:

|  | C | H |
|---|---|---|
| % calculated + ⅓ $H_2O$ | 73.83 | 5.68 |
| % found | 73.55 | 5.63 |

PREPARATION 68

1,2-Dihydro-1-acenaphthylenylmethylamine

Step A: 1,2-Dihydro-1-acenaphthylenone

In a 1 litre three-necked flask, oxalyl chloride (2.87 ml, $3.22.10^{-2}$ mol, 1 eq.) is added dropwise, under argon, to a solution of (naphth-1-yl)acetic acid (6 g, $3.22.10^{-2}$ mol) in anhydrous dichloromethane (270 ml) at 0° C. A few drops of anhydrous dimethylformamide are then added. After 1 hour at 0° C., slight evolution of gas is still observed and the three-necked flask is left at ambient temperature for 40 minutes. After return to 0° C., aluminium chloride (11.2 g, $8.38.10^{-2}$ mol, 2.6 eq.) is added gradually with a spatula. The solution is stirred for twenty minutes and becomes green-black in colour. The mixture is poured into an ice/1N HCl mixture. After separation of the phases and washings of the acidic aqueous phase with dichloromethane, the combined organic phases are washed with water, then treated with a saturated $NaHCO_3$ solution and finally washed with a saturated NaCl solution. After drying over $MgSO_4$ and evaporation under reduced pressure, the title product is obtained in the form of a yellow solid.

Melting point: 123° C.; Elemental microanalysis:

|  | C | H |
|---|---|---|
| % calculated | 85.69 | 4.79 |
| % found | 85.59 | 4.80 |

Step B: Ethyl2-(1,2-dihydro-1-acenaphthylenylidene)acetate

Triethyl phosphonoacetate (7.11 ml, $3.58.10^{-2}$ mol, 1.15 eq.) is added dropwise, under argon, to a suspension, in anhydrous THF (50 ml), of 60% sodium hydride in oil (1.43 g, $3.58.10^{-2}$ mol. 1.15 eq.), previously washed with pentane. After 40 minutes' stirring at ambient temperature, the compound obtained in Step A (5.24 g, $3.12.10^{-2}$ mol, 1 eq.), dissolved in anhydrous THF (55 ml), is added over 10 minutes. The reaction mixture is stirred for one night at ambient temperature, then diluted with water, filtered over Celite and extracted several times with ether. After drying over $MgSO_4$ and evaporation under reduced pressure, the oily residue is chromatographed on a silica gel column using $CH_2Cl_2$/petroleum ether 50/50. A mixture of the two E/Z isomers is isolated.

Elemental microanalysis:

|  | C | H |
|---|---|---|
| % calculated | 80.65 | 5.92 |
| % found | 80.68 | 5.97 |

Step C: Ethyl2-(1,2-dihydro-1-acenaphthylenyl)acetate 55 mg of $PdCl_2$ in 5 ml of methanol are treated with 25 mg of sodium borohydride. After 15 minutes' stirring, the compound obtained in Step B (1 g, $4.20.10^{-3}$ mol), diluted with methanol (25 ml), is added. The mixture is purged with argon and placed under a hydrogen atmosphere. After 2 hours 30 minutes' hydrogenation, the reaction mixture is filtered over Celite, rinsed and then evaporated under reduced pressure.

Step D: 2-(1,2-Dihydro-1-acenaphthylenyl)acetic Acid

The ester obtained in Step C (1.9 g, $7.91.10^{-3}$ mol) is heated at reflux in the presence of potassium hydroxide (2.34 g, $4.17.10^{-2}$ mol, 5.3 eq.), water (16 ml) and methanol (16 ml) for one night. After evaporating off the solvent, the residue is taken up in water and extracted twice with ether. The basic aqueous phase is acidified using concentrated HCl in the cold state. The acid is extracted with ethyl acetate and dried over $MgSO_4$. After evaporating off the solvent under reduced pressure, the title compound is obtained in the form of a yellow solid.

Melting point: 123° C.; Elemental microanalysis:

|  | C | H |
|---|---|---|
| % calculated | 79.23 | 5.70 |
| % found | 79.12 | 5.77 |

Step E: 1,2-Dihydro-1-acenaphthylenylmethylamine

In a 250 ml three-necked flask, triethylamine (3.49 ml, $2.50.10^{-2}$ mol, 1.15 eq.) is added dropwise to a solution, cooled to 0° C., of the acid obtained in Step D (4.62 g, $2.18.10^{-2}$ mol) in a mixture of acetone (95 ml) and water (5.4 ml). Ethyl chloroformate (2.71 ml, $2.83.10^{-2}$ mol, 1.30 eq.) is then slowly added at 0° C.; evolution of gas is visible. The mixture is stirred at 0° C. for 30 minutes; after it has been established, on TLC ($CH_2Cl_2$), that the starting material has disappeared, a solution of sodium azide (1.89 g, $2.83.10^{-2}$ mol, 1.30 eq.) in water (9.2 ml) is added at 0° C. The mixture is maintained at that temperature for one hour. The mixture is poured into an ice/water mixture and is then extracted with ether. The ethereal phases are washed with water, then dried over $Na_2SO_4$ and evaporated in vacuo without heating. The acyl azide is taken up in 50 ml of anhydrous toluene and then heated at 80° C. until nitrogen is no longer evolved. After evaporating off the toluene, the oil corresponding to the isocyanate is heated at 100° C. together with a 20% hydrochloric acid solution (52 ml) for 3 hours; the mixture is stirred for one night at ambient temperature. The reaction mixture is diluted with water, filtered through filter paper and extracted with ether. The aqueous phase of pH=1 is rendered basic using solid sodium carbonate and is then extracted three times with dichloromethane. The combined organic phases are washed with water and dried over $K_2CO_3$. After evaporating off the solvent under reduced pressure, the amine is obtained in the form of an oil (820 mg). The solid, having been filtered and taken up in dichloromethane, is treated in the same manner as the filtrate. The amine so obtained is converted into the hydrochloride after being solubilised in ether and treated with a 4N ethereal hydrogen chloride solution. After drying, the title product is obtained in the form of a white solid.

Melting point: >250° C.; Elemental microanalysis:

|  | C | H | N |
|---|---|---|---|
| % calculated | 71.07 | 6.42 | 6.37 |
| % found | 70.84 | 6.49 | 6.40 |

PREPARATION 69

(8-Methoxy-1,2-dihydro-1-acenaphthylenyl) methylamine

The procedure is as in Preparation 68, starting from (7-methoxynaphth-1-yl)acetic acid.

PREPARATION 70

1,2-Dihydro-1-acenaphthylenylethylamine

Step A: (1,2-Dihydro-1-acenaphthylenylidene) acetonitrile

The procedure is as in Step B of Preparation 68, with replacement of the triethyl phosphonoacetate with diethyl cyanomethylphosphonate.

Elemental microanalysis:

|  | C | H | N |
|---|---|---|---|
| % calculated | 87.93 | 4.74 | 7.32 |
| % found | 87.85 | 4.79 | 7.25 |

Step B: (1,2-Dihydro-1-acenaphthylenyl)acetonitrile

The catalyst is prepared starting from 55 mg of $PdCl_2$ in 5 ml of methanol treated with 25 mg of sodium borohydride. After 15 minutes' stirring, the compound obtained in Step A (1 g, $5.23.10^{-3}$ mol), diluted with methanol (15 ml), is incorporated. The mixture is purged with argon and placed under hydrogen. After 3 days' hydrogenation, the reaction mixture is filtered over Celite, rinsed and then evaporated under reduced pressure. The title product is isolated in the form of a light brown oil.

Elemental microanalysis:

|  | C | H | N |
|---|---|---|---|
| % calculated + ⅛ $H_2O$ | 86.01 | 5.80 | 7.16 |
| % found | 85.73 | 5.87 | 7.13 |

Step C: 1,2-Dihydro-1-acenaphthylenylethylamine

The nitrile obtained in Step B (900 mg, $4.66.10^{-3}$ mol), diluted with methanol (30 ml), is hydrogenated with vigorous stirring at ambient temperature in the presence of ammonium hydroxide (2 ml) and Raney nickel. After 23 hours, the starting material has disappeared. After filtering over Celite, then rinsing and evaporating off the solvent under reduced pressure, the title amine is obtained in the form of an oil, which is used without being purified.

PREPARATION 71

(8-Methoxy-1,2-dihydro-1-acenaphthylenyl) ethylamine

The procedure is as in Preparation 70.

Step A: (8-Methoxy-1,2-dihydro-1-acenaphthylenyl) acetonitrile

Step B: (8-Methoxy-1,2-dihydro-1-acenaphthylenyl) ethylamine

Elemental microanalysis:

|  | C | H | N |
|---|---|---|---|
| % calculated | 71.07 | 6.42 | 6.37 |
| % found | 70.84 | 6.49 | 6.40 |

PREPARATION 72

2-(1-Methoxy-7,8,9,10-tetrahydrocycloheptaldel naphthalen-7-ylidene)acetonitrile Step A: 3-(2-Methoxynaphth-1-yl)butenoic Acid A mixture of 2-methoxy-1-naphthaldehyde (2.45 g, $1.32.10^{-2}$ mol, 1 eq.) and (3-triphenyl-phosphonium) propanoic acid bromide (6 g, $1.44.10^{-2}$ mol, 1.1 eq.), solubilised in an anhydrous mixture of THF and DMSO (17 ml/17 ml), is added dropwise to a suspension, under argon at 0° C., in anhydrous THF (10 ml) of 60% sodium hydride in oil (1.16 g, $2.90.10^{-2}$ mol, 2.2 eq.), previously washed with pentane. The reaction mixture is stirred for one night at ambient temperature, then diluted with water, filtered over Celite and, after the addition of a few drops of sodium hydroxide solution, extracted twice with ether. The basic aqueous phase is acidified using HCl in the cold state. The desired acid is extracted with ether. After washing the ethereal phase with a saturated NaCl solution, then drying over $MgSO_4$ and evaporating under reduced pressure, the solid residue is chromatographed on a silica gel column (1. $CH_2Cl_2$; 2. $CH_2Cl_2/MeOH$:97/3). A white solid corresponding to the mixture of the two E/Z isomers of the title compound is obtained.

Melting point: 112° C.; Elemental microanalysis:

|  | C | H |
|---|---|---|
| % calculated | 74.36 | 5.82 |
| % found | 74.47 | 5.90 |

Step B: 4-(2-Methoxynaphth-1-yl)butanoic Acid

The compound obtained in Step A (3.4 g, $1.40.10^{-2}$ mol) is solubilised in ethyl acetate (90 ml) in the presence of 5% palladium-on-carbon. The mixture is purged with argon and placed under a hydrogen atmosphere. After 15 hours' hydrogenation, the reaction mixture is filtered over Celite, rinsed and then evaporated under reduced pressure. The title product is isolated in the form of white crystals.

Melting point: 88° C.; Elemental microanalysis:

|  | C | H |
|---|---|---|
| % calculated | 73.75 | 6.60 |
| % found | 73.59 | 6.71 |

Step C: 1-Methoxy-7,8,9,10-tetrahydrocyclohepta[de]naphthalen-7-one

The procedure is as in Step E of Preparation 1.

Melting point: 67° C.; Elemental microanalysis:

|  | C | H |
|---|---|---|
| % calculated | 79.62 | 6.24 |
| % found | 79.73 | 6.31 |

Step D: 2-(1-Methoxy-7,8,9,10-tetrahydrocyclohepta[de]naphthalen-7-ylidene)acetonitrile The procedure is as in Step A of Preparation 19.

Melting point: 96° C.; Elemental microanalysis:

|  | C | H | N |
|---|---|---|---|
| % calculated | 81.90 | 6.06 | 5.62 |
| % found | 81.88 | 6.18 | 5.64 |

EXAMPLE 1

N-[(4-Methoxy-2,3-dihydro-1H-1-phenalenyl)methyl]acetamide

In a 100 ml three-necked flask, the hydrochloride obtained in Preparation 1 (300 mg, $1.14.10^{-3}$ mol, 1 eq.) is solubilised in a two-phase $CH_2Cl_2$/water medium (17 ml/17 ml) in the presence of sodium carbonate (854 mg, $7.96.10^{-3}$ mol, 7 eq.). Acetic anhydride (110 µl, $1.17.10^{-3}$ mol, 1 eq.) is added at 0° C. The reaction mixture is stirred at ambient temperature for 20 minutes. After separation of the phases, washings of the organic phase with a saturated $NaHCO_3$ solution, water and then a saturated NaCl solution, drying over $MgSO_4$ and finally evaporating off the solvent under reduced pressure, the residue is chromatographed using flash chromatography (1. $CH_2Cl_2$; 2. $CH_2Cl_2$/MeOH: 99/1). The title compound is isolated in the pure form by recrystallisation from hexane/AcOEt.

Melting point: 126° C.; Elemental microanalysis:

|  | C | H | N |
|---|---|---|---|
| % calculated | 75.81 | 7.11 | 5.20 |
| % found | 75.64 | 7.19 | 5.15 |

EXAMPLE 2

N-[(4-Methoxy-2,3-dihydro-1H-phenalenyl)methyl]propionamide

The procedure is as in Example 1, with replacement of the acetic anhydride with propionic anhydride.

Melting point: 120° C.; Elemental microanalysis:

|  | C | H | N |
|---|---|---|---|
| % calculated | 76.30 | 7.47 | 4.94 |
| % found | 76.21 | 7.59 | 4.89 |

EXAMPLE 3

N-[(4-Methoxy-2,3-dihydro-1H-1-phenalenyl)methyl]cyclopropanecarboxamide

The hydrochloride obtained in Preparation 1 (382 mg, $1.45.10^{-3}$ mol) is taken up in dichloromethane and treated with ammonium hydroxide until the solid has been solubilised and a basic pH has been obtained for the aqueous phase. After separation of the phases, the amine is dried over $K_2CO_3$. At 0° C., the amine (320 mg, $1.41.10^{-3}$ mol) is taken up in anhydrous dichloromethane (10 ml) in the presence of triethylamine on potassium hydroxide (295 µl, $2.12.10^{-3}$ mol, 1.5 eq.). Cyclopropionyl chloride (130 µl, $1.43.10^{-3}$ mol, 1 eq.) is added dropwise at 0° C. The reaction mixture is stirred at ambient temperature for minutes. After washings with water, drying over $MgSO_4$ and then evaporating off the solvent under reduced pressure, the residue (400 mg) is chromatographed using flash chromatography (1. $CH_2Cl_2$; 2. $CH_2Cl_2$/MeOH: 99/1). The title product is obtained in the pure form by recrystallisation from hexane/AcOEt.

Melting point: 119° C.; Elemental microanalysis:

|  | C | H | N |
|---|---|---|---|
| % calculated | 77.26 | 7.17 | 4.74 |
| % found | 77.19 | 7.24 | 4.70 |

EXAMPLE 4

N-[(4-Methoxy-2,3-dihydro-1H-1-phenalenyl)methyl]butanamide

The procedure is as in Example 1, with replacement of the acetic anhydride with butanoic anhydride.

Melting point: 100° C.; Elemental microanalysis:

|  | C | H | N |
|---|---|---|---|
| % calculated | 76.74 | 7.80 | 4.71 |
| % found | 76.65 | 7.89 | 4.67 |

EXAMPLE 5

N-[(4-Methoxy-2,3-dihydro-1H-1-phenalenyl) methyl]-N-methyl-1-cyclopropanecarboxamide The compound obtained in Example 3 is reacted in the presence of NaH (1.5 eq) and dimethyl sulphate (1.2 eq). The reaction is monitored using TLC. When all the starting material has disappeared, the reaction mixture is hydrolysed and then extracted. After evaporating off the solvents, the title product is isolated by flash chromatography.

EXAMPLE 6

N-[(4-Hydroxy-2,3-dihydro-1H-1-phenalenyl) methyl]-N-methyl-cyclopropanecarboxamide The compound obtained in Example 3 is subjected to demethylation in the presence of a customary agent such as, for example, $BBr_3$.

EXAMPLE 7

N-[(4-Benzyloxy-2,3-dihydro-1H-1-phenalenyl) methyl]cyclopropanecarboxamide

The compound obtained in Example 6 is reacted in a basic system in the presence of benzyl chloride.

EXAMPLE 8

N-[(4-Allyloxy-2,3-dihydro-1H-1-phenalenyl) methyl]cyclopropane-carboxamide

The procedure is as in Example 7, with replacement of the benzyl chloride with allyl chloride.

EXAMPLE 9

N-Cyclobutyl-N'-[(4-methoxy-2,3-dihydro-1H-1-phenalenyl)methyl]-urea

The compound of Preparation 1 is suspended in pyridine; then cyclobutyl isocyanate is added dropwise and the reaction mixture is heated. When the reaction has ended, the reaction mixture is poured into ice-cold water and acidified using a 1N hydrochloric acid solution. After customary treatment, the title compound is isolated in the pure form.

EXAMPLE 10

N-(2,3-Dihydro-1H-1-phenalenylmethyl)-2-iodoacetamide

The procedure is as in Example 1, with 1-iodoacetic anhydride being condensed with the compound obtained in Preparation 2.

EXAMPLE 11

N-[(4-Methoxy-2,3-dihydro-1H-1-phenalenyl) methyl]benzamide

The procedure is as in Example 1, with replacement of the acetic anhydride with benzoic anhydride.

EXAMPLE 12

N-[(4,9-Dimethoxy-2,3-dihydro-H-1-phenalenyl) methyl]hexanamide

The procedure is as in Example 1, with hexanoic anhydride being condensed with the compound obtained in Preparation 3.

EXAMPLE 13

N-[(4-Ethyl-2,3-dihydro-1H-1-phenalenyl)methyl] cyclohexane-carboxamide

The procedure is as in Example 1, with cyclohexanecarboxylic anhydride being condensed with the compound obtained in Preparation 4.

EXAMPLE 14

N-[(4-Chloro-2,3-dihydro-1H-1-phenalenyl)methyl] heptanamide

The procedure is as in Example 1, with heptanoic anhydride being condensed with the compound obtained in Preparation 5.

EXAMPLE 15

N-[(4-Chloro-2,3-dihydro-1H-1-phenalenyl)methyl] acetamide

The procedure is as in Example 1, starting from the compound obtained in Preparation 5.

EXAMPLE 16

N-[(6-Methoxy-4,5-dihydro-3H-1-benzo[cd] isobenzofuran-5-yl)methyl]acetamide

The procedure is as in Example 1, starting from the compound obtained in Preparation 6.

EXAMPLE 17

N-[(6-Methoxy-4,5-dihydro-3H-benzo[cd] isobenzofuran-5-yl)-methyl] cyclohexanecarboxamide The procedure is as in Example 16, with replacement of the acetic anhydride with cyclohexanecarboxylic anhydride.

EXAMPLE 18

N-[(6-Metboxy-4,5-dihydro-3H-benzo[cd] isobenzofuran-3-yl)methyl]acetamide

The procedure is as in Example 1, starting from the compound obtained in Preparation 7.

EXAMPLE 19

N-[(6-Ethyl-4,5-dihydro-3H-benzo[cd] isobenzofuran-5-yl)methyl]pentanamide

The procedure is as in Example 1, with pentanoic anhydride being condensed with the compound obtained in Preparation 8.

EXAMPLE 20

N-[(6-Ethyl-4,5-dihydro-3H-benzo[cd] isobenzofuran-3-yl)methyl]butanamide

The procedure is as in Example 1, with butanoic anhydride being condensed with the compound obtained in Preparation 9.

EXAMPLE 21

N-[(6-Methoxy-4,5-dihydro-3H-naphthol[1,8-bc]
thiophen-5-yl)methyl]propanamide

The procedure is as in Example 2, starting from the compound obtained in Preparation 10.

EXAMPLE 22

N-[(6-Methoxy-4,5-dihydro-3H-naphthol[1.8-bc]
thiophen-3-yl)methyl]acetamide

The procedure is as in Example 1, starting from the compound obtained in Preparation 11.

EXAMPLE 23

N-[(6-Methoxy-4,5-dihydro-3H-naphtho[1,8-bc]
thiophen-3-yl)methyl]-N-methylacctamide The procedure is as in Example 5, starting from the compound obtained in Example 22.

EXAMPLE 24

N-[(6-Methoxy-4,5-dihydro-3H-naphtho[1,8-bc]
thiophen-3-yl)methyl]-N-methylethanethioamide The compound obtained in Example 23 is treated in customary manner with Lawesson's reagent.

EXAMPLE 25

N-Cyclobutyl-N'-[(6-methoxy-4,5-dihydro-3H-
naphtho[1,8-bc]-thiophen-3-yl)methyl]urea The procedure is as in Example 9, starting from the compound obtained in Preparation 11.

EXAMPLE 26

N-[(6-Methoxy-1,3,4,5-tetrahydrobenzo[cd]indol-3-
yl)methyl]acetamide

The procedure is as in Example 1, starting from the compound obtained in Preparation 12.

EXAMPLE 27

N-[(6-Methoxy-1-methyl-1,3,4,5-tetrahydrobenzo
[cd]indol-3-yl)methyl]-N-methylacetamide The compound obtained in Example 26, dissolved in tetrahydrofuran, is added dropwise at 0° C. to a suspension of NaH (2.2 eq.) in THF. Dimethyl sulphate (2.3 eq.) is added very slowly at 0° C. and then the reaction mixture is stirred at ambient temperature. When the reaction has ended, customary treatment is carried out and the title product is isolated by chromatography.

EXAMPLE 28

N-[(6-Hydroxy-1-methyl-1,3,4,5-tetrahydrobenzo
[cd]indol-3-yl)methyl]-N-methylacetamide The compound of Example 27, dissolved in dichloromethane, is added dropwise at 0° C. to a suspension of aluminium chloride and benzylthiol. The reaction is monitored by TLC. When the reaction has ended, the reaction mixture is poured onto ice and then acidified using 1N HCl. Customary extraction is carried out and the title compound is isolated by chromatography.

EXAMPLE 29

N-Methyl-N-1(1-methyl-6-(2-propynyloxy)-1,3,4,5-
tetrahydrobenzo-[cd]indol-3-yl)methyl]acetamide The procedure is as in Example 7, starting from the compound obtained in Example 28 and with replacement of the benzyl chloride with 3-chloro-1-propyne.

EXAMPLE 30

N-[(6-Methoxy-1,3,4,5-tetrahydro-3-
acenaphthylenyl)methyl]-1-
cyclopropanecarboxamide The procedure is as in Example 3, starting from the compound obtained in Preparation 13.

EXAMPLE 31

N-[(6-Hydroxy-1,3,4,5-tetrahydro-3-
acenaphthylenyl)methyl]-1-
cyclopropanecarboxamide The procedure is as in Example 6, starting from the compound obtained in Example 30.

EXAMPLE 32

N-[(6-Benzyloxy-1,3,4,5-tetrahydro-3-
acenaphthylenyl)methyl]-1-
cyclopropanecarboxamide The procedure is as in Example 7, starting from the compound obtained in Example 31.

EXAMPLE 33

N-[(7-Methoxy-2,3-dihydro-1H-cyclopenta[b]
naphthalen-1-yl)methyl]acetamide

The procedure is as in Example 1, starting from the compound obtained in Preparation 14.

EXAMPLE 34

N-(6,7-Dihydro-5H-indeno[5,6-b]thiophen-5-
ylmethyl)butanamide

The procedure is as in Example 1, with butanoic anhydride being condensed with the compound obtained in Preparation 15.

EXAMPLE 35

N-(7,8-Dihydro-6H-indeno[4,5-b]thiophen-6-
ylmethyl)acetamide

The procedure is as in Example 1, starting from the compound obtained in Preparation 16.

EXAMPLE 36

N-(7,8-Dihydro-6H-indeno[4,5-b]thiophen-8-
ylmethyl)acetamide

The procedure is as in Example 1, starting from the compound obtained in Preparation 17.

EXAMPLE 37

N-(7,8-Dihydro-6H-indeno[5,4,-b]thiophen-8-
ylmethyl)-2-chloroacetamide

The procedure is as in Example 1, with chloroacetic anhydride being condensed with the compound obtained in Preparation 18.

EXAMPLE 38

N-[2-(4-Methoxy-2,3-dihydro-1H-1-phenalenyl) ethyl]acetamide

The nitrile obtained in Step A of Preparation 19 (440 mg, $1.85.10^{-3}$ mol), diluted with tetrahydrofuran (12 ml), is hydrogenated at ambient temperature in the presence of acetic anhydride (430 µl, $4.56.10^{-3}$ mol, 2.5 eq.) and Raney nickel. After 8 hours' hydrogenation, the reaction mixture is filtered over Celite, rinsed and evaporated under reduced pressure. The residue is then taken up in dichloromethane and washed with water, then with a saturated $NaHCO_3$ solution and subsequently with water. After drying over $MgSO_4$ and evaporating off the solvent, the residue is purified by flash chromatography ($CH_2Cl_2$/methanol: 99/1). Elemental microanalysis:

|  | C | H | N |
|---|---|---|---|
| % calculated + ¼$H_2O$ | 75.10 | 7.53 | 4.87 |
| % found | 74.95 | 7.50 | 4.80 |

EXAMPLE 39

N-[2-(4-Methoxy-2,3-dihydro-1H-1-phenalenyl) ethyl]propanamide

The nitrile obtained in Step A of Preparation 19 (500 mg, $2.11.10^{-3}$ mol), in tetrahydro-furan (25 ml), is hydrogenated at ambient temperature in the presence of propionic anhydride (500 µl, $3.90.10^{-3}$ mol, 1.85 eq.) and Raney nickel. After 30 hours' hydrogenation, the reaction mixture is filtered over Celite, rinsed and evaporated under reduced pressure. The residue is then taken up in dichloromethane and washed with water, then with a saturated $NaHCO_3$ solution and subsequently with water. After drying over $MgSO_4$ and evaporating off the solvent, the residue having a weight of 650 mg is purified by flash chromatography ($CH_2Cl_2$/methanol: 99/1). Elemental microanalysis:

|  | C | H | N |
|---|---|---|---|
| % calculated + ¼$H_2O$ | 75.59 | 7.85 | 4.64 |
| % found | 75.54 | 7.88 | 4.61 |

EXAMPLE 40

N-[2-(4-Methoxy-2,3-dihydro-1H-1-phenalenyl) ethyl]-1-cyclopropanecarboxamide The hydrochloride obtained in Preparation 19 (350 mg, $1.26.10^{-3}$ mol) is taken up in a dichloromethane/water mixture (16 ml/16 ml) in the presence of sodium carbonate (940 mg). At 0° C., cyclopropionyl chloride (115 µl, $1.27.10^{-3}$ mol, 1 eq.) is added dropwise. The reaction mixture is stirred at ambient temperature for 15 minutes. Neutralisation is carried out by adding a few drops of ammonium hydroxide. After washings with water, drying over $MgSO_4$ and then evaporating off the solvent under reduced pressure, the residue is purified using flash chromatography (1. $CH_2Cl_2$; 2. $CH_2Cl_2$/MeOH: 99/1).

Melting point: 118° C.; Elemental microanalysis:

|  | C | H | N |
|---|---|---|---|
| % calculated + ¼$H_2O$ | 76.52 | 7.55 | 4.64 |
| % found | 76.55 | 7.51 | 4.42 |

EXAMPLE 41

N-[2-(4-Methoxy-2,3-dihydro-1H-1-phenalenyl) ethyl]-4-methoxybenzamide

The procedure is as in Example 40, with replacement of the cyclopropionyl chloride with 4-methoxy-benzoyl chloride.

EXAMPLE 42

N-[2-(4-Methoxy-2,3-dihydro-1H-1-phenalenyl) ethyl]-3-chlorobenzamide

The procedure is as in Example 41, with replacement of the cyclopropionyl chloride with 3-chloro-benzoyl chloride.

EXAMPLE 43

N-[2-(4-Methoxy-2,3-dihydro-1H-1-phenalenyl) ethyl]propanethioamide

The title compound is obtained by subjecting the compound of Example 39 to Lawesson's reagent.

EXAMPLE 44

N-[2-(4-Methoxy-2,3-dihydro-1H-1-phenalenyl) ethyl]-3-butenamide

The procedure is as in Example 40, with replacement of the propionyl chloride with butenoyl chloride.

EXAMPLE 45

N-[2-(4-Hydroxy-2,3-dihydro-1H-1-phenalenyl) ethyl]acetamide

The procedure is as in Example 6, starting from the compound obtained in Example 38.

EXAMPLE 46

N-[2-(4-Cyclopropyloxy-2,3-dihydro-1H-1-phenalenyl)ethyl]-acetamide

The procedure is as in Example 7, with replacement of the benzyl chloride with cyclopropyl chloride.

EXAMPLE 47

N-[2-(6-Methoxy-4,5-dihydro-3H-benzo[cd] isobenzofuran-5-yl)ethyl]butanamide The procedure is as in Example 38, with butanoyl chloride being condensed with the compound obtained in Preparation 20.

EXAMPLE 48

N-Butyl-N-[2-(6-methoxy-4,5-dihydro-3H-benzo [cd]isobenzofuran-5-yl)ethyl]acetamide The procedure is as in Example 5, starting from the compound of Example 38 and with replacement of the methyl sulphate with butyl iodide.

EXAMPLE 49

N-[2-(6-Chloro-4,5-dihydro-3H-benzo[cd]
isobenzofuran-5-yl)ethyl]-acetamide

The procedure is as in Example 38, starting from the compound obtained in Preparation 21.

EXAMPLE 50

N-[2-(6-Methoxy-4,5-dihydro-3H-benzo[cd]
isobenzofuran-3-yl)ethylibutanamide

The procedure is as in Example 47, starting from the compound obtained in Preparation 22.

EXAMPLE 51

N-Hexyl-N-[2-(6-methoxy-4,5-dihydro-3H-benzo
[cd]isobenzofuran-3-yl)ethyl]butanamide The procedure is as in Example 48, starting from the compound of Example 50 and with replacement of the butyl iodide with hexyl iodide.

EXAMPLE 52

N-[2-(6-Ethyl-4,5-dihydro-3H-naphtho[1,8-bc]
thiophen-3-yl)ethyl]heptanamide

The procedure is as in Example 38, with heptanoyl chloride being condensed with the compound obtained in Preparation 23.

EXAMPLE 53

N-[2-(6-Methoxy-1,3,4,5-tetrahydro-3-
acenaphthylenyl)ethyl]-1-cyclobutanecarboxamide The procedure is as in Example 38, with cyclobutanoyl chloride being condensed with the compound obtained in Preparation 24.

EXAMPLE 54

N-[2-(6-Methoxy-1,3,4,5-tetrahydrobenzo[cd]indol-
3-yl)ethyl]butanamide

The procedure is as in Example 47, starting from the compound obtained in Preparation 25.

EXAMPLE 55

N-[2-(6-Hydroxy-1,3,4,5-tetrahydrobenzo[cd]indol-
3-yl)ethyl]butanamide

The procedure is as in Example 28, starting from the compound obtained in Example 54.

EXAMPLE 56

N-[2-(1,3,4,5-Tetrahydrobenzo[cd]indol-3-yl)ethyl]
acetamide

The procedure is as in Example 38, starting from the compound obtained in Preparation 26.

EXAMPLE 57

N-Cyclobutyl-2-(4-methoxy-2,3-dihydro-1H-1-
phenalenyl)ethyl]acetamide

The title product is obtained by condensing N-cyclobutylamine with the acid obtained in Preparation 27 after conversion into the acid chloride.

EXAMPLE 58

N-Propyl-2-(4-methoxy-2,3-dihydro-1H-1-
phenalenyl)acetamide

The procedure is as in Example 57, with replacement of the N-cyclobutylamine with N-propylamine.

EXAMPLE 59

N-Hexyl-2-(4-chloro-2,3-dihydro-1H-1-phenalenyl)
ethyl]acetamide

The procedure is as in Example 57, with N-hexylamine being condensed with the acid chloride of the compound obtained in Preparation 28.

EXAMPLE 60

N-Phenyl-2-(6-chloro-4,5-dihydro-3H-benzo[cd]
isobenzofuran-5-yl)-ethyl]acetamide The procedure is as in Example 57, with N-phenylamine being condensed with the acid chloride of the compound obtained in Preparation 29.

EXAMPLE 61

N-(2,3,4-Trimethoxyphenyl-2-(6-methoxy-1 3,4,5-
tetrahydrobenzo-[cd]-indol-3-yl)acetamide The procedure is as in Example 57, with N-(2,3,4-trimethoxyphenyl)amine being condensed with the acid chloride of the compound obtained in Preparation 30.

EXAMPLE 62

N-Hexyl-2-(6-methoxy-1,3,4,5-tetrahydro-3-
acenaphthylenyl)-acetamide

The procedure is as in Example 59, starting from the compound obtained in Preparation 31.

EXAMPLE 63

N-[3-(4-Methoxy-2,3-dihydro-1H-1-phenalenyl)
propyl]pentanamide

The procedure is as in Example 19, starting from the compound obtained in Preparation 32.

EXAMPLE 64

N-Methyl-N-[3-(4-methoxy-2,3-dihydro-1H-1-
phenalenyl)propyl]pentanamide

The procedure is as in Example 23, starting from the compound obtained in Example 63.

EXAMPLE 65

N-[3-(4,9-Dimethoxy-2,3-dihydro-1H-1-phenalenyl)
propyl]acetamide

The procedure is as in Example 38, starting from the compound obtained in Preparation 33.

EXAMPLE 66

N-Cyclopentyl-4-(4-methoxy-2,3-dihydro-1H-1-
phenalenyl)butanamide

The procedure is as in Example 57, with N-cyclopentylamine being condensed with the acid chloride of the compound obtained in Preparation 34.

EXAMPLE 67

N-Cyclopentyl-N-methyl-4-(4-methoxy-2,3-dihydro-1H-1-phenalenyl)butanamide

The procedure is as in Example 64, starting from the compound obtained in Example 66.

EXAMPLE 68

N-[2-(2,2a,3,4-Tetrahydroindeno[7,1-bc]furan-4-yl)ethyl]-1-cyclopropanecarboxamide The procedure is as in Example 40, starting from the compound obtained in Preparation 35.

EXAMPLE 69

N-[2-(2,2a,3,4-Tetrahydroindeno[7,1-bc]thiophen-4-yl)ethyl]acetamide

The procedure is as in Example 38, starting from the compound obtained in Preparation 36.

EXAMPLE 70

N-[2-(I,6-Dimethoxy-7,8,9,10-tetrahydrocyclohepta[de]naphthalen-7-yl)ethyl]acetamide The procedure is as in Example 38, starting from the compound obtained in Preparation 37.

EXAMPLE 71

N-[(1-Methoxy-7,8,9,10-tetrahydrocyclohepta[de]naphthalen-7-yl)methyl]acetamide

The procedure is as in Example 38, starting from the compound obtained in Preparation 38.

EXAMPLE 72

N-(6,7,8,9-Tetrahydro-2-thiabenzo[cd]azulen-9-yl)methyl]acetamide

The procedure is as in Example 19, starting from the compound obtained in Preparation 39.

EXAMPLE 73

N-[(5-Methoxy-6,7,8,9-tetrahydro-2-oxabenzo[cd]azulen-9-yl)methyl]propionamide

The procedure is as in Example 2, starting from the compound obtained in Preparation 40.

EXAMPLE 74

N-(7-Methoxy-1,2,3,4-tetrahydro-1-anthracenyl)acetamide

The procedure is as in Example 1, starting from the compound obtained in Preparation 41.

EXAMPLE 75

N-(6-Methoxy-1,2,3,4-tetrahydro-1-anthracenyl)acetamide

The procedure is as in Example 1, starting from the compound obtained in Preparation 42.

EXAMPLE 76

N-(5,6,7,8-Tetrahydronaphtho[2,3-b]thiophen-5-yl)-1-cyclopropylcarboxamide

The procedure is as in Example 3, starting from the compound obtained in Preparation 43.

EXAMPLE 77

N-(3-Ethyl-5,6,7,8-tetrahydronaphtho[2,3-b]thiophen-5-yl)heptanamide

The procedure is as in Example 14, starting from the compound obtained in Preparation 44.

EXAMPLE 78

N-(6,7,8,9-Tetrahydronaphtho[1,2-b]thiophen-6-yl)acetamide

The procedure is as in Example 1, starting from the compound obtained in Preparation 45.

EXAMPLE 79

N-(6,7,8,9-Tetrahydronaphtho[1,2-b]thiophen-9-yl)acetamide

The procedure is as in Example 1, starting from the compound obtained in Preparation 46.

EXAMPLE 80

N-(6,7,8,9-Tetrahydronaphtho[2,1-b]thiophen-9-yl)-1-cyclohexanecarboxamide

The procedure is as in Example 13, starting from the compound obtained in Preparation 47.

EXAMPLE 81

N-(6,7,8,9-Tetrahydronaphtho[2,1-b]thiophen-9-yl)-2,2,2-trifluoroacetamide

The procedure is as in Example 1, starting from the compound obtained in Preparation 47 and with replacement of the acetic anhydride with trifluoroacetic anhydride.

EXAMPLE 82

N-(1-Methoxy-6,7,8,9-tetrahydronaphtho[2-b]thiophen-9-yl)methyl]acetamide

The procedure is as in Example 1, starting from the compound obtained in Preparation 48.

EXAMPLE 83

N-(1-Methoxy-6,7,8,9-tetrahydronaphtho[2,1-b]thiophen-9-yl)methyl]acetamide

The procedure is as in Example 2, starting from the compound obtained in Preparation 49.

EXAMPLE 84

N-[(3-Methoxy-2,3-dihydro-1H-1-phenalenyl)methyl]acetamide

The procedure is as in Example 1, starting from the compound obtained in Preparation 50.

EXAMPLE 85

N-[3-(3,8-Dimethoxy-1,2-dihydro-1-acenaphthylenyl)propyl]-2,2,2-trifluoroacetamide The procedure is as in Example 63, with acetyl chloride being condensed with the compound obtained in Preparation 51.

EXAMPLE 86

N-Pentyl-4-(3,8-dimethoxy-1,2-dihydro-1-acenaphthylenyl)butanamide

The procedure is as in Example 66, with N-pentylamine being condensed with the acid chloride of the compound obtained in Preparation 52.

EXAMPLE 87

N-[(4-Methoxy-2,3-dihydro-1H-2-phenalenyl)methyl]acetamide

The procedure is as in Example 1, starting from the compound obtained in Preparation 53.

EXAMPLE 88

N-[(4-Methoxy-2,3-dihydro-1H-2-phenalenyl)methyl]-1-cyclobutanecarboxamide

The procedure is as in Example 1, starting from the compound obtained in Preparation 53 and with replacement of the acetic anhydride with cyclobutanecarboxylic anhydride.

EXAMPLE 89

N-[(4-Hydroxy-2,3-dihydro-1H-2-phenalenyl)methyl]-1-cyclobutanecarboxamide

The procedure is as in Example 6, starting from the compound obtained in Example 88.

EXAMPLE 90

N-[(4-Benzyloxy-2,3-dihydro-1H-2-phenalenyl)methyl]-1-cyclobutanecarboxamide

The procedure is as in Example 7, starting from the compound obtained in Example 89.

EXAMPLE 91

N-[(4-Allyfoxy-2,3-dihydro-1H-2-phenalenyl)methyl]-1-cyclobutanecarboxamide

The procedure is as in Example 8, starting from the compound obtained in Example 89.

EXAMPLE 92

N-[(4-Methoxy-2,3-dihydro-1H-2-phenalenyl)methyl]ethanethioamide

The procedure is as in Example 24, starting from the compound obtained in Example 87.

EXAMPLE 93

N-[(4-Ethyl-2,3-dihydro-1H-2-phenalenyl)methyl]propanamide

The procedure is as in Example 2, starting from the compound obtained in Preparation 54.

EXAMPLE 94

N-Cyclopropyl-2-(4,9-dimethoxy-2,3-dihydro-1H-2-phenalenyl)acetamide

The procedure is as in Example 57, with N-cyclopropylamine being condensed with the acid chloride obtained in Preparation 55.

EXAMPLE 95

N-Methyl-4-methoxy-2,3-dihydro-1H-2-phenalenecarboxamide

The procedure is as in Example 57, with N-methylamine being condensed with the acid chloride obtained in Preparation 56.

EXAMPLE 96

N-[2-(4-Methoxy-2,3-dihydro-1H-2-phenalenyl)ethyl]heptanamide

The procedure is as in Example 52, starting from the compound obtained in Preparation 57.

EXAMPLE 97

N-Methyl-N-[2-(4-methoxy-2,3-dihydro-1H-2-phenalenyl)ethyl]heptanamide

The procedure is as in Example 5, starting from the compound obtained in Example 96.

EXAMPLE 98

N-[3-(4-Methoxy-2,3-dihydro-1H-2-phenalenyl)propyl]acetamide

The procedure is as in Example 38, starting from the compound obtained in Preparation 58.

EXAMPLE 99

N-[(6-Chloro-2,3-dihydro-1H-2-phenalenyl)methyl]acetamide

The procedure is as in Example 1, starting from the compound obtained in Preparation 59.

EXAMPLE 100

N-[(1,6-Dimethoxy-7,8,9,10-tetrahydrocyclohepta[de]naphthalen-8-yl)methyl]acetamide The procedure is as in Example 1, starting from the compound obtained in Preparation 60.

EXAMPLE 101

N-[(1,6-Dimethoxy-7,8,9,10-tetrahydrocyclohepta[de]naphthalen-8-yl)methyl]-1-cyclopropanecarboxamide The procedure is as in Example 3, starting from the compound obtained in Preparation 60.

EXAMPLE 102

N-Ethyl-1,6-dimethoxy-7,8,9,10-tetrahydrocyclohepta[de]-naphthalene-8-carboxamide The procedure is as in Example 57, with N-ethylamine being condensed with the acid chloride obtained in Preparation 61.

EXAMPLE 103

N-(8-Methoxy-1,2-dihydro-1-acenaphthylenyl)acetamide

The procedure is as in Example 1, starting from the compound obtained in Preparation 62.

Melting point: 217–219° C.

The compounds of Examples 104 and 105 are obtained by the action of HBr on the compound obtained in Example 84.

EXAMPLE 104

N-[(3-Hydroxy-2,3-dihydro-1H-1-phenalenyl)methyl]acetamide

EXAMPLE 105

N-[(3-Bromo-2,3-dihydro-1H-1-phenalenyl)methyl]acetamide

EXAMPLE 106

N-[(3-Oxo-2,3-dihydro-1H-1-phenalenyl)methyl]acetamide

The title compound is obtained by customary oxidation of the alcohol obtained in Example 104.

EXAMPLE 107

N-[(4-Methoxy-2,3-dihydro-1H-1-phenalenyl)methyl]butanamide

The amine obtained in Preparation 1 (400 mg, $1.76.10^{-3}$ mol, 1 eq.) is diluted with anhydrous dichloromethane (12 ml) in the presence of triethylamine (368 μl, $2.64.10^{-3}$ mol. 1.5 eq.). At 0° C., butanoyl chloride (183 μl, $1.76.10^{-3}$ mol, 1 eq.) is added slowly. The reaction mixture is stirred at ambient temperature for 40 minutes. After separation of the phases, washings of the organic phase with a saturated $NaHCO_3$ solution, water and then a saturated NaCl solution, and drying over $MgSO_4$ and finally evaporating off the solvent under reduced pressure, the residue is purified using flash chromatography (1. $CH_2Cl_2$; 2. $CH_2Cl_2$/MeOH: 99/1). The title compound is obtained in the form of a white solid by recrystallisation from a hexane/AcOEt mixture.

Melting point: 100° C.; Elemental microanalysis:

|  | C | H | N |
|---|---|---|---|
| % calculated | 76.74 | 7.80 | 4.71 |
| % found | 76.65 | 7.89 | 4.67 |

EXAMPLE 108

N-[2-(9-Methoxy-2,3-dihydro-1H-1-phenalenyl)ethyl]acetamide

The nitrile obtained in Preparation 63 (219 mg, 9.23.104 mol), dissolved in tetrahydrofuran (22 ml), is hydrogenated at ambient temperature in the presence of acetic anhydride (174 μl, $1.85.10^{-3}$ mol, 2 eq.) and Raney nickel. After 4 hours' hydrogenation, the reaction mixture is filtered over Celite, rinsed and evaporated under reduced pressure. The residue is then taken up in dichloromethane and washed with water, then with a saturated $NaHCO_3$ solution and subsequently with water. After drying over $MgSO_4$ and evaporating off the solvent, the residue is purified using flash chromatography (AcOEt/petroleum ether: 30/50) and recrystallised from a cyclohexane/AcOEt mixture. The title product is isolated in the form of a white solid.

Melting point: 98° C.; Elemental microanalysis:

|  | C | H | N |
|---|---|---|---|
| % calculated | 76.30 | 7.47 | 4.94 |
| % found | 76.13 | 7.60 | 4.79 |

EXAMPLE 109

N-[2-(9-Methoxy-2,3-dihydro-1H-1-phenalenyl)ethyl]butanamide

The procedure is as in Example 108, with replacement of the acetic anhydride with butyric anhydride. The title product is isolated in the form of an oil.

EXAMPLE 110

N-[2-(4-Methoxy-2,3-dihydro-1H-1-phenalenyl)ethyl]butanamide

In a 100 ml three-necked flask, the hydrochloride obtained in Preparation 19 (300 mg, $1.08.10^{-3}$ mol. 1 eq.) is solubilised in a two-phase $CH_2Cl_2$/water medium (12 ml/12 ml) in the presence of sodium carbonate (801 mg, $7.56.10^{-3}$ mol, 7 eq.). Butanoyl chloride (112 μl, 1.08.10mol, 1 eq.) is added at 0° C. The reaction mixture is stirred at ambient temperature for 20 minutes. After separation of the phases, washing of the organic phase with a saturated $NaHCO_3$ solution, $H_2O$ and then a saturated NaCl solution, then drying over $MgSO_4$ and finally evaporating off the solvent under reduced pressure, the residue is purified using flash chromatography (1. $CH_2Cl_2$; 2. $CH_2Cl_2$/MeOH: 99/1). The title product is isolated in the form of an oil.

EXAMPLE 111

N-[2-(4,9-Dimethoxy-2,3-dihydro-1H-1-phenalenyl)ethyl]propanamide

The procedure is as in Example 108, starting from the amine obtained in Preparation 64 and with replacement of the acetic anhydride with propionic anhydride. The title product obtained is isolated in the form of a white solid.

Melting point: 111° C.; Elemental microanalysis:

|  | C | H | N |
|---|---|---|---|
| % calculated | 73.37 | 7.70 | 4.28 |
| % found | 73.45 | 7.87 | 4.18 |

EXAMPLE 112

N-[2-(4,9-Dimethoxy-2,3-dihydro-1H-1-phenalenyl)ethyl]butanamide

The procedure is as in Example 111, with replacement of the propionic anhydride with butyric anhydride. The title product obtained is isolated in the form of a white solid.

Melting point: 99° C.; Elemental microanalysis:

|  | C | H | N |
|---|---|---|---|
| % calculated + ⅛H₂O | 73.39 | 7.99 | 4.08 |
| % found | 73.12 | 8.16 | 3.97 |

EXAMPLE 113

N-[2-(4,9-Dimethoxy-2,3-dihydro-1H-1-phenalenyl)ethyl]-1-cyclopropanecarboxamide At 0° C., cyclopropanoyl chloride (67 μl, $7.37.10^{-3}$ mol, 1 eq.) is added to a solution of the amine obtained in Preparation 64 (200 mg, 7.57.104 mol, 1 eq.) in a dichloromethane/water mixture (10 ml/10 ml) in the presence of sodium carbonate (547mg, $5.16.10^{-3}$ mol, 7 eq.). The reaction mixture is stirred at ambient temperature for 15 minutes. Neutralisation is carried out by adding a few drops of ammonium hydroxide. After washing with water, drying over MgSO₄ and then evaporating off the solvent under reduced pressure, the residue is purified by flash chromatography (AcOEt/petroleum ether 40/60). The title product is isolated in the form of a white solid by recrystallisation from a cyclohexane/AcOEt mixture.

Melting point: 120° C.; Elemental microanalysis:

|  | C | H | N |
|---|---|---|---|
| % calculated | 74.31 | 7.42 | 4.13 |
| % found | 74.17 | 7.57 | 4.05 |

EXAMPLE 114

N-[2-(4,9-Dimethoxy-2,3-dihydro-1H-1-phenalenyl)ethyl]acetamide

The procedure is as in Example 111, with replacement of the propionic anhydride with acetic anhydride. The title product is isolated in the form of a white solid.

Melting point: 125° C.; Elemental microanalysis:

|  | C | H | N |
|---|---|---|---|
| % calculated | 72.82 | 7.40 | 4.47 |
| % found | 72.68 | 7.60 | 4.35 |

EXAMPLE 115

N-[2-(9-Methoxy-2,3-dihydro-1H-1-phenalenyl)methyl]acetamide

In a 50 ml three-necked flask, the amine obtained in Preparation 65 (172 mg, 7.57.10 mol, 1 eq.) is solubilised in a two-phase CH₂Cl₂/water medium (9 ml/9 ml) in the presence of sodium carbonate (561 mg, $5.30.10^{-3}$ mol, 7 eq.). Acetic anhydride (72 μl, $7.57.10^{-3}$ mol, 1 eq.) is added at 0° C. The reaction mixture is stirred at ambient temperature for 20 minutes. After separation of the phases, washings of the organic phase with a saturated NaHCO₃ solution, H20 and a saturated NaCl solution, then drying over MgSO₄ and finally evaporating off the solvent under reduced pressure, the residue (180 mg) is purified using flash chromatography (AcOEt/petroleum ether, 40/60). The title product is isolated in the form of a white solid by recrystallisation from a cyclohexane/AcOEt mixture.

Melting point: 192° C.; Elemental microanalysis:

|  | C | H | N |
|---|---|---|---|
| % calculated | 75.81 | 7.11 | 5.20 |
| % found | 75.43 | 7.35 | 5.12 |

EXAMPLE 116

N-[2-(9-Methoxy-2,3-dihydro-1H-1-phenalenyl)methyl]butanamide

The procedure is as in Example 115, with replacement of the acetic anhydride with butanoyl chloride. The title product is isolated in the form of a white solid.

Melting point:114° C.; Elemental microanalysis:

|  | C | H | N |
|---|---|---|---|
| % calculated | 76.74 | 7.80 | 4.71 |
| % found | 76.52 | 8.02 | 4.55 |

EXAMPLE 117

N-[2-(4,9-Dimethoxy-2,3-dihydro-1H-1-phenalenyl)methyl]acetamide

The procedure is as in Example 115, starting from the amine obtained in Preparation 3. The title product is isolated in the form of a white solid.

Melting point: 184° C.; Elemental microanalysis:

|  | C | H | N |
|---|---|---|---|
| % calculated | 72.22 | 7.07 | 4.68 |
| % found | 71.85 | 7.30 | 4.52 |

EXAMPLE 118

N-[2-(4,9-Dimethoxy-2,3-dihydro-1H-1-phenalenyl)methyl]propanamide

The procedure is as in Example 117, with replacement of the acetic anhydride with propanoyl chloride. The title product is isolated in the form of a white solid.

Melting point: 158° C.; Elemental microanalysis:

|  | C | H | N |
|---|---|---|---|
| % calculated | 72.82 | 7.40 | 4.47 |
| % found | 72.61 | 7.55 | 4.39 |

EXAMPLE 119

N-[2-(4,9-Dimethoxy-2,3-dihydro-1H-1-phenalenyl)methyl]butanamide

The procedure is as in Example 117, with replacement of the acetic anhydride with butanoyl chloride. The title product is isolated in the form of a white solid.

Melting point: 140° C.; Elemental microanalysis:

|  | C | H | N |
|---|---|---|---|
| % calculated | 73.37 | 7.70 | 4.23 |
| % found | 73.15 | 7.80 | 4.14 |

Separation of the two enantiomers is carried out on a chiral column: $[\alpha]_D$ (589 nm, T=23° C.) F enantiomer 1=−22°+2 (CHCl$_3$, 5 mg/ml) enantiomer 2=+20°+2 (CHCl$_3$, 5 mg/ml)

EXAMPLE 120

N-[2-(4,9-Dimethoxy-2,3-dihydro-1H-1-phenalenyl) methyl]-1-cyclopropanecarboxamide The procedure is as in Example 117, with replacement of the acetic anhydride with cyclopropanoyl chloride. The title product is isolated in the form of a white solid.

Melting point: 192° C.; Elemental microanalysis:

|  | C | H | N |
|---|---|---|---|
| % calculated | 73.82 | 7.12 | 4.30 |
| % found | 73.62 | 7.27 | 4.18 |

EXAMPLE 121

(E)-N-Methyl-2-(4-methoxy-2,3-dihydro-1H-1-phenalenylidene)acetamide

The acid obtained in Preparation 66 (250 mg, $9.84.10^{-4}$ mol, 1 eq.) is solubilised in anhydrous dichloromethane (20 ml). At 0° C., under argon, triethylamine on potassium hydroxide (164 µl, $1.18.10^{-3}$ mol, 1.2 eq.) is added, followed by isobutyl chloroformate (153 µl, $1.18.10^{-3}$ mol, 1.2 eq.). Complete formation of the anhydride starting from the acid is carried out at 0° C. in 1 hour 10 minutes. Separately, methylamine hydrochloride (199 mg, $2.95.10^{-3}$ mol, 3 eq.) is stirred under argon together with anhydrous dichloromethane (18 ml) and triethylamine (411 µl, $2.95.10^{-3}$ mol, 3 eq.). After 10 minutes' stirring, the resulting suspension is added to the reaction mixture and stirring is continued for one night at ambient temperature. After one washing with water and drying over magnesium sulphate, the filtrate is evaporated to dryness under reduced pressure. Purification on a silica gel column (dichloromethane/methanol, 98/2) followed by recrystallisation from an AcOEt/cyclohexane mixture allows the title product to be isolated in the form of a beige solid.

Melting point: 174° C.; Elemental microanalysis:

|  | C | H | N |
|---|---|---|---|
| % calculated | 76.38 | 6.41 | 5.24 |
| % found | 76.10 | 6.39 | 5.18 |

EXAMPLE 122

(Z)-N-Methyl-2-(4-methoxy-2,3-dihydro-1H-1-phenalenylidene)acetamide

The procedure is as in Example 121, starting from the acid obtained in Preparation 67.

Melting point: 175° C.; Elemental microanalysis:

|  | C | H | N |
|---|---|---|---|
| % calculated + ⅛H$_2$O | 75.74 | 6.45 | 5.20 |
| % found | 75.72 | 6.55 | 5.06 |

EXAMPLE 123

N-(1,2-Dihydro-1-acenaphthylenylmethyl)acetamide

In a 100 ml three-necked flask, the hydrochloride obtained in Preparation 68 (550 mg, $2.50.10^{-3}$ mol, 1 eq.) is solubilised in a two-phase CH$_2$Cl$_2$/water medium (20 ml/20 ml) in the presence of sodium carbonate (1.86 g, $1.75.10^{-2}$ mol, 7 eq.). Acetic anhydride (236 µl, $2.50.10^{-3}$ mol, 1 eq.) is added at 0° C. The reaction mixture is stirred at ambient temperature for 20 minutes. After separation of the phases, washings of the organic phase with a saturated NaHCO$_3$ solution, H$_2$O and a saturated NaCl solution, then drying over MgSO$_4$ and finally evaporating off the solvent under reduced pressure, the residue having a weight of 500 mg is purified using flash chromatography (1. CH$_2$Cl$_2$; 2. CH$_2$Cl$_2$/MeOH: 99/1).

The title product is isolated in the form of a white solid by recrystallisation from a cyclohexane/AcOEt mixture.

Melting point: 145° C.; Elemental microanalysis:

|  | C | H | N |
|---|---|---|---|
| % calculated | 79.97 | 6.71 | 6.22 |
| % found | 79.83 | 6.82 | 6.15 |

EXAMPLE 124

N-(1,2-Dihydro-1-acenaphthylenylmethyl) propanamide

The procedure is as in Example 123, with replacement of the acetic anhydride with propionic anhydride. The title product is isolated in the form of a white solid.

Melting point 111° C. Elemental microanalysis:

|  | C | H | N |
|---|---|---|---|
| % calculated | 80.30 | 7.16 | 5.85 |
| % found | 80.15 | 7.28 | 5.70 |

EXAMPLE 125

N-(1,2-Dihydro-1-acenaphthylenylmethyl) butanamide

The procedure is as in Example 123, with replacement of the acetic anhydride with butanoyl chloride. The title product is isolated in the form of a white solid.

Melting point: 111° C.; Elemental microanalysis:

|  | C | H | N |
|---|---|---|---|
| % calculated | 80.57 | 7.56 | 5.53 |
| % found | 80.02 | 7.70 | 5.40 |

EXAMPLE 126

N-(1,2-Dihydro-1-acenaphthylenylmethyl)-1-cyclopropanecarboxamide

The procedure is as in Example 123, with replacement of the acetic anhydride with cyclopropanoyl chloride.

Melting point: 146° C.; Elemental microanalysis:

|  | C | H | N |
|---|---|---|---|
| % calculated | 81.24 | 6.82 | 5.57 |
| % found | 81.13 | 6.88 | 5.52 |

EXAMPLE 127

N-(8-Methoxy-1,2-dihydro-1-acenaphthylmethyl) acetamide

In a 100 ml three-necked flask, the amine obtained in Preparation 69 (385 mg, $1.81.10^{-3}$ mol, 1 eq.) is solubilised in a two-phase $CH_2Cl_2$/water medium (20 ml/20 ml) in the presence of sodium carbonate (1.34 g, $1.26.10^{-2}$ mol, 7 eq.). Acetic anhydride (170 µl, $1.81.10^{-3}$ mol, 1 eq.) is added at 0° C. The reaction mixture is stirred at ambient temperature for 40 minutes. After separation of the phases, washing of the organic phase with a saturated $NaHCO_3$ solution, $H_2O$ and a saturated NaCl solution, then drying over $MgSO_4$ and finally evaporating off the solvent under reduced pressure, the residue having a weight of 360 mg is purified using flash chromatography (1. $CH_2Cl_2$; 2. $CH_2Cl_2$/MeOH: 99/1). The title product is isolated in the form of a white solid by recrystallisation from a cyclohexane/AcOEt mixture.

Melting point: 148° C.; Elemental microanalysis:

|  | C | H | N |
|---|---|---|---|
| % calculated + ½$H_2O$ | 72.70 | 6.86 | 5.30 |
| % found | 72.08 | 6.86 | 5.24 |

EXAMPLE 128

N-(8-Methoxy-1,2-dihydro-1-acenaphthylmethyl) propanamide

The procedure is as in Example 127, with replacement of the acetic anhydride with propionic anhydride.

Melting point: 160° C.; Elemental microanalysis:

|  | C | H | N |
|---|---|---|---|
| % calculated + ½$H_2O$ | 73.35 | 7.24 | 5.03 |
| % found | 73.88 | 7.25 | 5.15 |

EXAMPLE 129

N-(8-Methoxy-1,2-dihydro-1-acenaphthylmethyl)-1-cyclopropanecarboxamide

The procedure is as in Example 127, with replacement of the acetic anhydride with cyclopropanoyl chloride.

Melting point: 185° C.; Elemental microanalysis:

|  | C | H | N |
|---|---|---|---|
| % calculated + ¼$H_2O$ | 75.63 | 6.88 | 4.90 |
| % found | 75.78 | 6.98 | 4.93 |

EXAMPLE 130

N-(8-Methoxy-1,2-dihydro-1-acenaphthylmethyl) butanamide

The procedure is as in Example 127, with replacement of the acetic anhydride with butanoyl chloride. The title product is obtained in the form of a white solid.

Melting point: 146° C.; Elemental microanalysis:

|  | C | H | N |
|---|---|---|---|
| % calculated | 76.30 | 7.47 | 4.94 |
| % found | 76.12 | 7.51 | 4.93 |

The two enantiomers are separated on a chiral column:

$$[\alpha]_D(589\ nm,\ T = 23°\ C.) \begin{cases} \text{enantiomer 1} = -20° \pm 2(CHCl_3,\ 5\ mg/ml) \\ \text{enantiomer 2} = +18° \pm 2(CHCl_3,\ 5\ mg/ml) \end{cases}$$

EXAMPLE 131

N-[2-(1,2-Dihydro-1-acenaphthyl)ethyl]acetamide

The nitrile obtained in Step B of Preparation 70 (230 mg, $1.20.10^{-3}$ mol), diluted with tetrahydrofuran (25 ml), is hydrogenated at ambient temperature in the presence of acetic anhydride (200 µl, $2.12.10^{-3}$ mol, 1.8 eq.) and Raney nickel. After 5 hours' hydrogenation, the reaction mixture is filtered over Celite, rinsed and evaporated under reduced pressure. The residue is then taken up in dichloromethane and washed with water, then with a saturated $NaHCO_3$ solution and subsequently with water. After drying over $MgSO_4$ and evaporating off the solvent, the residue is purified by flash chromatography ($CH_2Cl_2$/methanol: 99/1).

Melting point: 116° C.; Elemental microanalysis:

|  | C | H | N |
|---|---|---|---|
| % calculated | 80.30 | 7.10 | 5.85 |
| % found | 80.11 | 7.23 | 5.89 |

EXAMPLE 132

N-[2-(1,2-Dihydro-1-acenaphthyl)ethyl] propanamide

The procedure is as in Example 131, with replacement of the acetic anhydride with propionic anhydride.

Melting point: 100° C.; Elemental microanalysis:

|  | C | H | N |
|---|---|---|---|
| % calculated | 80.57 | 7.56 | 5.53 |
| % found | 80.34 | 7.54 | 5.50 |

EXAMPLE 133

N-[2-(1,2-Dihydro-1-acenaphthyl)ethyl]butanamide

The procedure is as in Example 131, with replacement of the acetic anhydride with butyric anhydride. The title product is isolated in the form of a white solid.

Melting point: 98° C.; Elemental microanalysis:

|  | C | H | N |
|---|---|---|---|
| % calculated | 80.86 | 7.92 | 5.24 |
| % found | 80.86 | 7.96 | 5.21 |

EXAMPLE 134

N-[2-(1,2-Dihydro-1-acenaphthyl)ethyl] cyclopropanecarboxamide

At 0° C., under argon, the amine obtained in Preparation 70 (500 mg, 2.53.10$^{-3}$ mol, 1 eq.) is solubilised in anhydrous dichloromethane (17 ml) in the presence of triethylamine (530 µl, 3.80.10$^{-3}$ mol, 1.5 eq.). Cyclopropanoyl chloride (230 µl, 2.53.10$^{-3}$ mol 1 eq.) is added dropwise at 0° C. The reaction mixture is stirred at ambient temperature for 20 minutes. After washings with water and with a saturated NaCl solution, and drying over MgSO$_4$ and then evaporating off the solvent under reduced pressure, the residue is recrystallised from a cyclohexane/AcOEt mixture.

Melting point: 159° C.;

EXAMPLE 135

N-[2-(8-Methoxy-1,2-dihydro-1-acenaphthyl)ethyl] acetamide

The procedure is as in Example 131, starting from the nitrile obtained in Step A of Preparation 71. The title product is isolated in the form of a white solid.

Melting point: 118° C.; Elemental microanalysis:

|  | C | H | N |
|---|---|---|---|
| % calculated | 80.30 | 7.10 | 5.85 |
| % found | 80.11 | 7.23 | 5.89 |

EXAMPLE 136

N-[2-(8-Methoxy-1,2-dihydro-1-acenaphthyl)ethyl] propanamide

The procedure is as in Example 135, with replacement of the acetic anhydride with propionic anhydride.

Melting point: 100° C.; Elemental microanalysis:

|  | C | H | N |
|---|---|---|---|
| % calculated | 80.57 | 7.56 | 5.53 |
| % found | 80.34 | 7.54 | 5.50 |

EXAMPLE 137

N-[2-(8-Methoxy-1,2-dihydro-1-acenaphthyl)ethyl] butanamide

The procedure is as in Example 135, with replacement of the acetic anhydride with butyric anhydride.

Melting point: 98° C.; Elemental microanalysis:

|  | C | H | N |
|---|---|---|---|
| % calculated | 80.86 | 7.92 | 5.24 |
| % found | 80.86 | 7.96 | 5.21 |

EXAMPLE 138

N-[2-(8-Methoxy-1,2-dihydro-1-acenaphthyl)ethyl]-1-cyclopropanecarboxamide

The procedure is as in Example 134, starting from the amine obtained in Preparation 71.

Melting point: 159° C.;

EXAMPLE 139

N-[2-(1-Methoxy-7,8,9,10-tetrahydrocyclohepta[de]naphthalen-7-ylidene)ethyl]propanamide The nitrile obtained in Preparation 72 (465 mg, 1.87.10$^{-3}$ mol), diluted with tetrahydrofuran (25 ml), is hydrogenated at ambient temperature in the presence of propionic anhydride (480 µl, 3.74.10$^{-3}$ mol, 2 eq.) and Raney nickel. After 24 hours' hydrogenation, the reaction mixture is filtered over Celite, rinsed and evaporated under reduced pressure. The residue is then taken up in dichloromethane and washed with water, then with a saturated NaHCO$_3$ solution and subsequently with water. After drying over MgSO$_4$ and evaporating off the solvent, the residue is purified using flash chromatography (1. CH$_2$Cl$_2$; 2. CH$_2$Cl$_2$/MeOH: 99/1). The title product is isolated in the form of a white solid.

E isomer:

The E isomer is obtained in the pure form by recrystallisation of the solid obtained above, which corresponds to the E/Z mixture, from an AcOEt/cyclohexane mixture.

Melting point: 131° C.; Elemental microanalysis:

|  | C | H | N |
|---|---|---|---|
| % calculated | 77.64 | 7.49 | 4.53 |
| % found | 77.28 | 7.54 | 4.36 |

PHARMACOLOGICAL STUDY

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$ (dose that causes the death of 50% of the animals) was evaluated and demonstrated the low toxicity of the compounds of the invention.

EXAMPLE B

Melatonin Receptor Binding Study on Pars Tuberalis Cells of Sheep

Melatonin receptor binding studies of the compounds of the invention were carried out according to conventional techniques on pars tuberalis cells of sheep, the pars tuberalis of to the adenohypophysis being characterised in mammals by a high density of melatonin receptors (Journal of Neuroendocrinology, 1, pp 1–4, 1989).

Protocol

1) Sheep pars tuberalis membranes are prepared and used as target tissue in saturation experiments to determine the binding capacities and affinities for 2-[$^{125}$I]-iodomelatonin.
2) Sheep pars tuberalis membranes are used as target tissue in competitive binding experiments using the various test compounds in comparison with melatonin. Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

Melatonin $mt_1$ and $MT_2$ Receptor Binding Study

The $mt_1$ or $MT_2$ receptor binding experiments are carried out using 2-[$^{125}$I]-melatonin as reference radioligand. The radioactivity retained is determined using a Beckman® LS 6000 liquid scintillation counter.

Competitive binding experiments are then carried out in triplicate using the various test compounds. A range of different concentrations is tested for each compound. The results enable the binding affinities of the compounds tested ($IC_{50}$) to be determined.

The $IC_{50}$ values found for the compounds of the invention show that the binding of the compounds tested is very strong for one or other of the $mt_1$ and $MT_2$ receptor sub-types, the values being in a range from 0.1 to 10 nM.

EXAMPLE D

Four Plate Test

The products of the invention are administered by the oesophageal route to groups each comprising ten mice. One group is given syrup of gum. Thirty minutes after administration of the products to be studied, the animals are placed in cages in which the floor is composed of four metal plates. Each time the animal passes from one plate to another it receives a light electric shock (0.35 mA). The number of passages from one plate to another in one minute is recorded. After administration, the compounds of the invention significantly increase the number of passages from one plate to another, demonstrating the anxiolytic activity of the compounds of the invention.

EXAMPLE E

Action of the Compounds of the Invention on the Circadian Rhythms of Locomotive Activity of the Rat The involvement of melatonin in influencing, by day/night alternation, the majority of physiological, biochemical and behavioural circadian rhythms has made it possible to establish a pharmacological model for research into melatoninergic ligands.

The effects of the molecules are tested in relation to numerous parameters and, in particular, in relation to the circadian rhythms of locomotive activity, which represent a reliable marker of the activity of the endogenous circadian clock. In this study, the effects of such molecules on a particular experimental model, namely the rat placed in temporal isolation (permanent darkness), are evaluated.

Experimental Protocol

One-month-old Long Evans male rats are subjected, as soon as they arrive at the laboratory, to a light cycle of 12 hours of light per 24 hours (LD 12: 12). After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12: 12, the rats are placed in permanent darkness (DD).

Two to three weeks later, when the free course (rhythm reflecting that of the endogenous clock) is clearly established, the rats are given a daily administration of the molecule to be tested.

The observations are made by means of visualisation of the rhythms of activity:

influence on the rhythms of activity by the light rhythm, disappearance of the influence on the rhythms in permanent darkness, influence by the daily administration of the molecule; transitory or long-lasting effect.

A software package makes it possible:

to measure the duration and intensity of the activity, the period of the rhythm of the animals during free course and during treatment, possibly to demonstrate by spectral analysis the existence of circadian and non-circadian (for example ultradian) components.

Results:

The compounds of the invention clearly appear to allow powerful action on the circadian rhythm via the melatoninergic system.

EXAMPLE F

Anti-arrhythmic Activity

Protocol (Ref: LAWSON J. W. et al. J. Pharmacol. Expert. Therap., 1968, 160, pp 22–31)

The test substance is administered intraperitoneally to a group of 3 mice 30 minutes before they are subjected to anaesthesia with chloroform. The animals are then observed for 15 minutes. The absence of recording of arrhythmia and of cardiac frequencies higher than 200 beats/min (control: 400–480 beats/min) in at least two animals indicates significant protection.

EXAMPLE G

Pharmaceutical Composition: Tablets

| | |
|---|---|
| 1000 tablets each comprising 5 mg of [(4-methoxy-2,3-dihydro-1H-phenalenyl)-methyl]propionamide (Example 2) | 5 g |
| wheat starch | 20 g |
| maize starch | 20 g |
| lactose | 30 g |
| magnesium stearate | 2 g |
| silica | 1 g |
| hydroxypropyl cellulose | 2 g |

We claim:
1. A compound of formula (I):

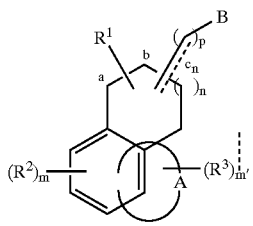

(I)

wherein:

A forms with the group to which it is bonded a tricyclic system selected from $A_1$, $A_2$, $A_3$ and $A_4$:

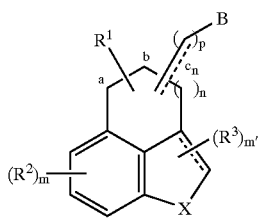

($A_1$)

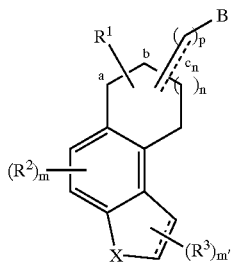

($A_2$)

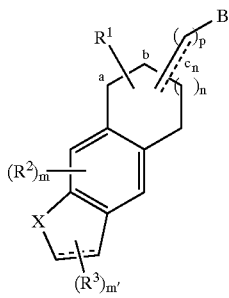

($A_3$)

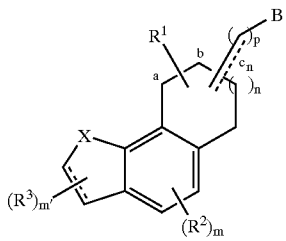

($A_4$)

$R^1$ represents hydrogen, halogen or linear or branched ($C_1$–$C_6$)alkyl, linear or branched ($C_1$–$C_6$)alkoxy, hydroxy or oxo, $R^2$ and $R^3$, which may be the same or different, represent halogen or $R_a$, $OR_a$, $COR_a$, $OCOR_a$ or $COOR_a$ (wherein $R_a$ represents hydrogen, optionally substituted linear or branched ($C_1$–$C_6$)alkyl, linear or branched ($C_1$–$C_6$)trihaloalkyl, optionally substituted linear or branched ($C_2$–$C_6$)alkenyl, optionally substituted linear or branched ($C_2$–$C_6$)alkynyl, optionally substituted ($C_3$–$C_8$)-cycloalkyl, optionally substituted ($C_3$–$C_8$)cycloalkyl-($C_1$–$C_6$)alkyl in which the alkyl moiety is linear or branched, or optionally substituted aryl), the symbols $(R^2)_m$ and $(R^3)_{m'}$ denote that the ring in question may be substituted by from 1 to 3 groups (which may be the same or different) belonging to the definitions for $R^2$ and $R^3$, X, when A represents a tricyclic system $A_1$, $A_2$, $A_3$ or $A_4$, represents sulphur, $(CH_2)_q$ (wherein q is 1 or 2), —CH═CH—, or $NR^4$ (wherein $R^4$ represents hydrogen or optionally substituted linear or branched ($C_1$–$C_6$)alkyl), or X represents oxygen when A represents the tricyclic system $A_1$, n is an integer such that $0 \leq n \leq 3$ p is an integer such that $1 \leq p \leq 3$ when n is 1, 2 or 3 and the

chain is in the b position and A represents either $A_2$, $A_3$ or $A_4$ wherein X represents —CH═CH—, or $A_1$, and such that $0 \leq p \leq 3$ in all other cases, it being possible for the

chain to be unsubstituted or substituted by one or more groups, which may be the same or different, selected from $R_a$, $OR_a$, $COR_a$, $COOR_a$ or halogen, B represents:

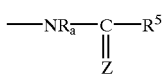

wherein $R_a$ is as defined hereinbefore, Z represents oxygen or sulphur,
and $R^5$ represents $R_a$ or $NR^6R^7$ wherein $R^6$ and $R^7$, which may be the same or different, represent $R_a$, or

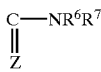

wherein Z, $R^6$ and $R^7$ are as defined hereinbefore,
the symbol ⋯⋯ denotes that the bond may be single or double provided that the valency of the atoms is respected,
it being understood that the symbol

is used to denote the formula

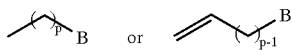

(in which case p is other than 0),
with the proviso that:
when the tricyclic group of formula $A_1$ is a 6-methoxytetrahydrobenzo[cd]indole, B cannot represent NHCOMe,
the compound of formula (I) cannot represent N-(4-methyl-2,3-dihydro-1H-1-phenalenyl)-1-cyclopropanecarboxamide, N-(4-methyl-2,3-dihydro-1H-1-phenalenyl)-2-chloroacetamide, 2-methyl-1,3,4,5-tetrahydrobenzo[cd]indole-3-carboxamide, N-(5-hydroxy-1,2,2a,3,4,5-hexahydro-4-acenaphthylenyl)acetamide, N-(5-hydroxy-1,2,2a,3,4,5-hexahydro-4-acenaphthylenyl)benzamide or N-(1,2,2a,3,4,5-hexahydro-4-acenaphthylenyl)acetamide,
it being understood that:
"aryl" is used to denote phenyl or naphthyl each optionally substituted by one or more groups, which may be the same or different, selected from hydroxy, linear or branched ($C_1$–$C_6$)alkoxy, linear or branched ($C_1$–$C_6$)alkyl, cyano, nitro, amino, trihaloalkyl, or halogen,
the expression "optionally substituted" applied to the terms "alkyl", "alkenyl" and "alkynyl" denotes that those groups may be substituted by one or more groups, which may be the same or different, selected from hydroxy, linear or branched ($C_1$–$C_6$)-alkoxy, aryl, or halogen,
the expression "optionally substituted" applied to the terms "cycloalkyl" and "cycloalkylalkyl" denotes that the cyclic moiety may be substituted by one or more groups, which may be the same or different, selected from hydroxy, linear or branched ($C_1$–$C_6$) alkoxy, oxo, or halogen,
their enantiomers and diastereoisomers, and addition salts thereof with a pharmaceutically acceptable acid or base.

2. A compound of formula (I) according to claim 1 represented by formula ($I_A$):

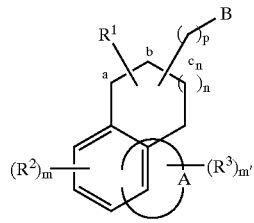

wherein:
A forms with the group to which it is bonded a tricyclic system selected from $A'_1$, $A'_2$, $A'_3$ and $A'_4$:

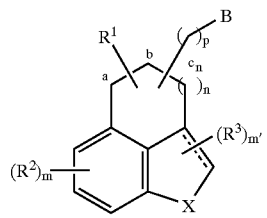

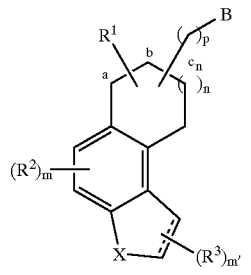

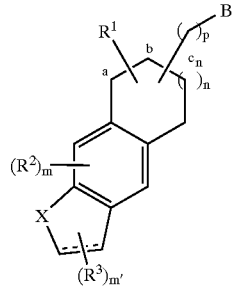

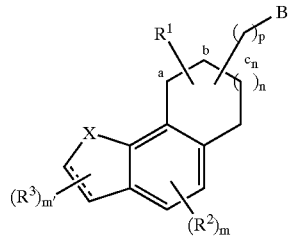

$R^1$ represents hydrogen, halogen or linear or branched ($C_1$–$C_6$)alkyl, linear or branched ($C_1$–$C_6$)alkoxy, hydroxy or oxo,
$R^2$ and $R^3$, which may be the same or different, represent halogen or $R_a$, $OR_a$, $COR_a$, $OCOR_a$ or $COOR_a$ (wherein $R_a$ represents hydrogen, optionally substituted linear or branched ($C_1$–$C_6$)alkyl, linear or branched ($C_1$–$C_6$)trihaloalkyl, an optionally substituted linear or branched ($C_2$–$C_6$)alkenyl, optionally substituted linear or branched ($C_2$–$C_6$)alkynyl, optionally substituted ($C_3$–$C_8$)cycloalkyl, optionally substituted ($C_3$–$C_8$)cycloalkyl-($C_1$–$C_6$)alkyl in which the alkyl moiety is linear or branched, or optionally substituted aryl), the symbols $(R^2)_m$ and $(R^3)_{m'}$ denote that the ring in question may be substituted by from 1 to 3 groups (which may be the same or different) belonging to the definitions for $R^2$ and $R^3$, X, when A represents a tricyclic system $A'_1$, $A'_2$, $A'_3$ or $A'_4$, represents sulphur, $(CH_2)_q$ (wherein q is 1 or 2), —CH=CH—, or $NR^4$ (wherein $R^4$ represents hydrogen or optionally substituted linear or branched ($C_1$–$C_6$)alkyl), or X represents oxygen when A represents the tricyclic system $A'_1$, n is an integer such that $0 \leq n \leq 3$ p is an integer such that $1 \leq p \leq 3$ when n is 1, 2 or 3 and the —$(CH_2)_p$—B chain is in the b position and A represents either a group $A'_2$, $A'_3$ or $A'_4$ wherein X represents —CH=CH, or $A'_1$, and such that $0 \leq p \leq 3$ in all other cases, it being possible for the $(CH_2)_p$ chain to be unsubstituted or substituted by one or more groups, which may be the same or different, selected from $R_a$, $OR_a$, $COR_a$, $COOR_a$ or halogen, B represents:

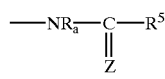

wherein $R_a$ is as defined hereinbefore, Z represents oxygen or sulphur, and $R^5$ represents $R_a$ or $NR^6R^7$ wherein $R^6$ and $R^7$, which may be the same or different, represent $R_a$, or

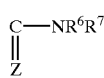

wherein Z, $R^6$ and $R^7$ are as defined hereinbefore, the symbols ....... denotes that the bond may be single or double provided that the valency of the atoms is respected, with the proviso that:

when the tricyclic group of formula $A'_1$ is a 6-methoxytetrahydrobenzo[cd]indole, B cannot represent NHCOMe, the compound of formula (I) cannot represent N-(4-methyl-2,3-dihydro-1H-1-phenalenyl)-1-cyclopropanecarboxamide, N-(4-methyl-2,3-dihydro-1H-1-phenalenyl)-2-chloroacetamide, 2-methyl-1,3,4,5-tetrahydrobenzo[cd]indole-3-carboxiamide, N-(5-hydroxy-1,2,2a,3,4,5-hexahydro-4-acenaphthylenyl)acetamide, N-(5-hydroxy-1,2,2a,3,4,5-hexahydro-4-acenaphthylenyl)benzamide or N-(1,2,2a,3,4,5-hexahydro-4-acenaphthylenyl)acetamide, it being understood that:

"aryl" is used to denote phenyl or naphthyl each optionally substituted by one or more groups, which may be the same or different, selected from hydroxy, linear or branched ($C_1$–$C_6$)alkoxy, linear or branched ($C_1$–$C_6$)alkyl, cyano, nitro, amino, trihaloalkyl, or halogen, the expression "optionally substituted" applied to the terms "alkyl", "alkenyl" and "alkynyl" denotes that those groups may be substituted by one or more groups, which may be the same or different, selected from hydroxy, linear or branched ($C_1$–$C_6$)-alkoxy, aryl, or halogen, the expression "optionally substituted" applied to the terms "cycloalkyl" and "cycloalkylalkyl" denotes that the cyclic moiety may be substituted by one or more groups, which may be the same or different, selected from hydroxy, linear or branched ($C_1$–$C_6$) alkoxy, oxo, or halogen, their enantiomers and diastereoisomers, and addition salts thereof with a pharmaceutically acceptable acid or base.

3. A compound of formula (I) according to claim 1 represented by formula ($I_B$):

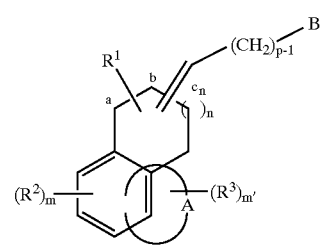

wherein:

A forms with the group to which it is bonded a tricyclic system selected from $A''_1$, $A''_2$, $A''_3$ and $A''_4$:

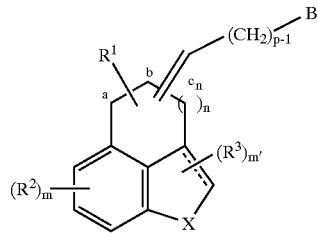

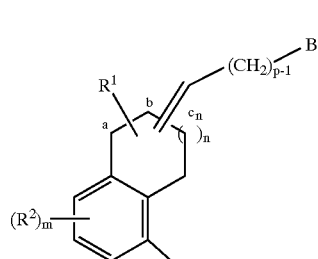

-continued (A"$_3$)
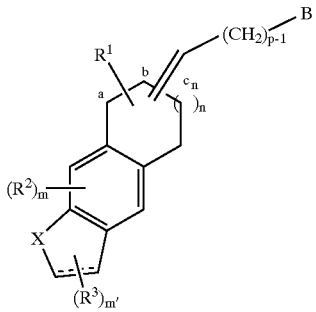

(A"$_4$)
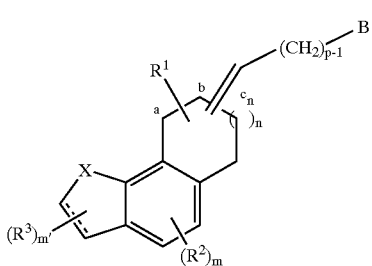

$R^1$ represents hydrogen, halogen or linear or branched ($C_1$–$C_6$)alkyl, linear or branched ($C_1$–$C_6$)alkoxy, hydroxy or oxo, $R^2$ and $R^3$, which may be the same or different, represent halogen or $R_a$, $OR_a$, $COR_a$, $OCOR_a$ or $COOR_a$ (wherein $R_a$ represents hydrogen, optionally substituted linear or branched ($C_1$–$C_6$)alkyl, linear or branched ($C_1$–$C_6$)trihaloalkyl, optionally substituted linear or branched ($C_2$–$C_6$)alkenyl, optionally substituted linear or branched ($C_2$–$C_6$)alkynyl, optionally substituted ($C_3$–$C_8$)cycloalkyl, optionally substituted ($C_3$–$C_8$)cycloalkyl-($C_1$–$C_6$)alkyl in which the alkyl moiety is linear or branched, or optionally substituted aryl), the symbols $(R^2)_m$ and $(R^3)_{m'}$ denote that the ring in question may be substituted by from 1 to 3 groups (which may be the same or different) belonging to the definitions for $R^2$ and $R^3$, X, when A represents a tricyclic system A"$_1$, A"$_2$, A"$_3$ or A"$_4$, represents sulphur, $(CH_2)_q$ (wherein q is 1 or 2), —CH=CH—, or $NR^4$ (wherein $R^4$ represents hydrogen or optionally substituted linear or branched ($C_1$–$C_6$)alkyl), or X represents oxygen when A represents the tricyclic system A"$_1$, n is an integer such that $0 \leq n \leq 3$ p is an integer such that $1 \leq p \leq 3$ it being possible for the

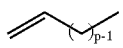

chain to be unsubstituted or substituted by one or more groups, which may be the same or different, selected from $R_a$, $OR_a$, $COR_a$, $COOR_a$ or halogen, B represents:

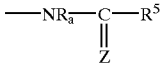

wherein $R_a$ is as defined hereinbefore, Z represents oxygen or sulphur, and $R^5$ represents $R_a$ or $NR^6R^7$ wherein $R^6$ and $R^7$, which may be the same or different, represent $R_a$, or

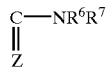

wherein Z, $R^6$ and $R^7$ are as defined hereinbefore, the symbol ...... denotes that the bond may be single or double provided that the valency of the atoms is respected, it being understood that:
"aryl" is used to denote phenyl or naphthyl each optionally substituted by one or more groups, which may be the same or different, selected from hydroxy, linear or branched ($C_1$–$C_6$)alkoxy, linear or branched ($C_1$–$C_6$)alkyl, cyano, nitro, amino, trihaloalkyl, or halogen, the expression "optionally substituted" applied to the terms "alkyl", "alkenyl" and "alkynyl" denotes that those groups may be substituted by one or more groups, which may be the same or different, selected from hydroxy, linear or branched ($C_1$–$C_6$)-alkoxy, aryl, or halogen, the expression "optionally substituted" applied to the terms "cycloalkyl" and "cycloalkylalkyl" denotes that the cyclic moiety may be substituted by one or more groups, which may be the same or different, selected from hydroxy, linear or branched ($C_1$–$C_6$) alkoxy, oxo, or halogen, their enantiomers and diastereoisomers, and addition salts thereof with a pharmaceutically acceptable acid or base.

4. A compound of formula (I) according to claim 1 wherein A forms with the groups to which it is bonded a tricyclic system of formula $A_1$, their enantiomers and diastereoisomers, and addition salts thereof with a pharmaceutically acceptable acid or base.

5. A compound of formula (I) according to claim 1 wherein A forms with the groups to which it is bonded a tricyclic system of formula $A_2$, $A_3$ or $A_4$, their enantiomers and diastereoisomers, and addition salts thereof with a pharmaceutically acceptable acid or base.

6. A compound of formula (I) according to claim 1 wherein A forms with the group to which it is bonded a tricyclic system of formula $A_1$ wherein X represents $(CH_2)_q$ or —CH=CH—, their enantiomers and diastereoisomers, and addition salts thereof with a pharmaceutically acceptable acid or base.

7. A compound of formula (I) according to claim 1 wherein A forms with the group to which it is bonded a tricyclic system of formula $A_1$ wherein X represents oxygen, their enantiomers and diastereoisomers, and addition salts thereof with a pharmaceutically acceptable acid or base.

8. A compound of formula (I) according to claim 1 wherein A forms with the group to which it is bonded a tricyclic system of formula $A_1$ wherein X represents sulphur, their enantiomers and diastereoisomers, and addition salts thereof with a pharmaceutically acceptable acid or base.

9. A compound of formula (I) according to claim 1 wherein A forms with the group to which it is bonded a tricyclic system of formula $A_1$ wherein X represents $NR^4$, their enantiomers and diastereoisomers, and addition salts thereof with a pharmaceutically acceptable acid or base.

10. A compound of formula (I) according to claim 1 wherein n represents an integer 0, 1 or 2, their enantiomers and diastereoisomers, and addition salts thereof with a pharmaceutically acceptable acid or base.

11. A compound of formula (I) according to claim 1 wherein A forms with the groups to which it is bonded a tricyclic system of formula $A_1$ wherein n is 0, 1 or 2, their enantiomers and diastereoisomers, and addition salts thereof with a pharmaceutically acceptable acid or base.

12. A compound of formula (I) according to claim 1 wherein A forms with the group to which it is bonded a 2,3-dihydrophenalene, 1,2-dihydroacenaphthylene or 7,8,9,10-tetrahydrocyclohepta[de]naphthalene tricyclic system, their enantiomers and diastereoisomers, and addition salts thereof with a pharmaceutically acceptable acid or base.

13. A compound of formula (I) according to claim 1 wherein p represents an integer 0, 1 or 2, their enantiomers and diastereoisomers, and addition salts thereof with a pharmaceutically acceptable acid or base.

14. A compound of formula (I) according to claim 1 wherein $R^2$ and $R^3$, which may be the same or different, represent an alkoxy or alkyl group or hydrogen, their enantiomers and diastereoisomers, and addition salts thereof with a pharmaceutically acceptable acid or base.

15. A compound of formula (I) according to claim 1 wherein $R^1$ represents hydrogen, their enantiomers and diastereoisomers, and addition salts thereof with a pharmaceutically acceptable acid or base.

16. A compound of formula (I) according to claim 1 wherein the

chain is in the a or c position, their enantiomers and diastereoisomers, and addition salts thereof with a pharmaceutically acceptable acid or base.

17. A compound of formula (I) according to claim 1 wherein the

chain is in the a or c position and p represents an integer 0 (in which case the bond ........ is single), 1 or 2, their enantiomers and diastereoisomers, and addition salts thereof with a pharmaceutically acceptable acid or base.

18. A compound of formula (I) according to claim 1 wherein B represents $NHCOR^5$, their enantiomers and diastereoisomers, and addition salts thereof with a pharmaceutically acceptable acid or base.

19. A compound of formula (I) according to claim 1 wherein B represents $CONHR^6$, their enantiomers and diastereoisomers, and addition salts thereof with a pharmaceutically acceptable acid or base.

20. A compound of formula (I) according to claim 1 wherein A forms with the group to which it is bonded a 2,3-dihydrophenalene, 1,2-dihydroacenaphthylene or 7,8,9,10-tetrahydrocyclohepta[de]naphthalene tricyclic system, each unsubstituted or substituted on the naphthalene moiety by one or more alkoxy or alkyl groups, and substituted in the a or c position by

wherein B represents $NHCOR^5$ or $CONHR^6$ group, their enantiomers and diastereoisomers, and addition salts thereof with a pharmaceutically acceptable acid or base.

21. A compound of formula (I) according to claim 1 wherein A forms with the group to which it is bonded a 1,2-dihydroacenaphthylene or 7,8,9,10-tetrahydrocyclohepta[de]naphthalene tricyclic system, each unsubstituted or substituted on the naphthalene moiety by one or two alkoxy groups and substituted in the a or c position by =CH—B, =CH—CH$_2$—B, —B, —CH$_2$—B or —(CH$_2$)$_2$—B wherein B represents $NHCOR^5$ or $CONHR^6$, their enantiomers and diastereoisomers, and addition salts thereof with a pharmaceutically acceptable acid or base.

22. A compound of formula (I) according to claim 1 wherein A forms with the group to which it is bonded a 2,3-dihydrophenalene tricyclic system, unsubstituted or substituted on the naphthalene moiety by one or two alkoxy groups and substituted in the a or c position by =CH—B, =CH—CH$_2$—B, —CH$_2$—B or —(CH$_2$)$_2$—B wherein B represents $NHCOR^5$ or $CONHR^6$, their enantiomers and diastereoisomers, and addition salts thereof with a pharmaceutically acceptable acid or base.

23. Compounds of formula (I) according to claim 1 which are: N-[(4-methoxy-2,3-dihydro-1H-1-phenalenyl)methyl] acetamide, N-[(4-methoxy-2,3-dihydro-1H-phenalenyl) methyl]propionamide, N-[(4-methoxy-2,3-dihydro-1H-1-phenalenyl)methyl]-cyclopropanecarboxamide, N-[(4-methoxy-2,3-dihydro-1H-1-phenalenyl)methyl]-butanamide, N-[(4-methoxy-2,3-dihydro-1H-1-phenalenyl) methyl]butanamide, N-[2-(9-methoxy-2,3-dihydro-1H-1-phenalenyl)methyl]acetamide, N-[2-(9-methoxy-2,3-dihydro-1H-1-phenalenyl)methyl]butanamide, N-[2-(4,9-dimethoxy-2,3-dihydro-1H-1-phenalenyl)methyl] acetamide, N-[2-(4,9-dimethoxy-2,3-dihydro-1H-1-phenalenyl)-methyl]propanamide, N-[2-(4,9-dimethoxy-2,3-dihydro-1H-1-phenalenyl)methyl]-butanamide and N-[2-(4,9-dimethoxy-2,3-dihydro-1H-1-phenalenyl)methyl]-1-cyclopropanecarboxamide, their enantiomers and diastereoisomers, and addition salts thereof with a pharmaceutically acceptable acid or base.

24. Compounds of formula (I) according to claim 1 which are: N-[2-(4-methoxy-2,3-dihydro-1H-1-phenalenyl)ethyl] acetamide, N-[2-(4-methoxy-2,3-dihydro-1H-1-phenalenyl) ethyl]propanamide, N-[2-(4-methoxy-2,3-dihydro-1H-1-phenalenyl)-ethyl]-1-cyclopropanecarboxamide, N-[2-(9-methoxy-2,3-dihydro-1H-1-phenalenyl)-ethyl]acetamide, N-[2-(9-methoxy-2,3-dihydro-1H-1-phenalenyl)ethyl] butanamide, N-[2-(4-methoxy-2,3-dihydro-1H-1-phenalenyl)ethyl]butanamide, N-[2-(4,9-di-methoxy-2,3-dihydro-1H-1-phenalenyl)ethyl]propanamide, N-[2-(4,9-dimethoxy-2,3-dihydro-1H-1-phenalenyl)ethyl]butanamide, N-[2-(4,9-dimethoxy-2,3-dihydro-1H-1-phenalenyl)ethyl]-1-cyclopropanecarboxamide and N-[2-(4,9-dimethoxy-2,3-dihydro-1H-1-phenalenyl)ethyl]acetamide, their enantiomers and diastereoisomers, and addition salts thereof with a pharmaceutically acceptable acid or base.

25. Compound of formula (I) according to claim 1 which is N-(8-methoxy-1,2-dihydro-1-acenaphthylenyl)acetamide, its enantiomers and diastereoisomers, and addition salts thereof with a pharmaceutically acceptable acid or base.

26. Compounds of formula (I) according to claim 1 which are: (E)-N-methyl-2-(4-methoxy-2,3-dihydro-1H-1-phenalenylidene)acetamide and (Z)-N-methyl-2-(4-methoxy-2,3-dihydro-1H-1-phenalenylidene)acetamide, their enantiomers and diastereoisomers, and addition salts thereof with a pharmaceutically acceptable acid or base.

27. Compounds of formula (I) according to claim 1 which are: N-(1,2-dihydro-1-acenaphthylenylmethyl)acetamide, N-(1,2-dihydro-1-acenaphthylenylmethyl)propanamide, N-(1,2-dihydro-1-acenaphthylenylmethyl)butanamide, N-(1,2-dihydro-1-acenaphthylenylmethyl)-1-cyclopropanecarboxamide, N-(8-methoxy-1,2-dihydro-1-acenaphthylmethyl)acetamide, N-(8-methoxy-1,2-dihydro-1-acenaphthylmethyl)-propanamide, N-(8-methoxy-1,2-dihydro-1-acenaphthylmethyl)-1-cyclopropanecarboxamide and N-(8-methoxy-1,2-dihydro-1-acenaphthylmethyl) butanamide, their enantiomers and diastereoisomers, and addition salts thereof with a pharmaceutically acceptable acid or base.

28. Compounds of formula (I) according to claim 1 which are: N-[2-(1,2-dihydro-1-acenaphthyl)ethyl]acetamide, N-[2-(1,2-dihydro-1-acenaphthyl)ethyl]propanamide, N-[2-(1,2-dihydro-1-acenaphthyl)ethyl]butanamide, N-[2-(1,2-dihydro-1-acenaphthyl)ethyl]cyclopropanecarboxamide, N-[2-(8-methoxy-1,2-dihydro-1-acenaphthyl)ethyl]acetamide, N-[2-(8-methoxy-1,2-dihydro-1-acenaphthyl)ethyl]propanamide, N-[2-(8-methoxy-1,2-dihydro-1-acenaphthyl)ethyl]butanamide and N-[2-(8-methoxy-1,2-dihydro-1-acenaphthyl)ethyl]-1-cyclopropanecarboxamide, their enantiomers and diastereoisomers, and addition salts thereof with a pharmaceutically acceptable acid or base.

29. A compound of formula (I) according to claim 1 which is N-[2-(1-methoxy-7,8,9,10-tetrahydrocyclohepta[de]naphthalen-7-ylidene)ethyl]propanamide, its enantiomers and diastereoisomers, and addition salts thereof with a pharmaceutically acceptable acid or base.

30. A method for treating a living body afflicted with disorders of the melatoninergic system comprising the step of administering to the living body an amount of a compound of claims 1 to 29 which is effective for the alleviation for said condition.

31. A pharmaceutical composition useful for treating melatoninergic disorders comprising, as active principle an effective amount of a compound as claimed in claims 1 to 29, together with one or more pharmaceutically acceptable excipients or vehicles.

* * * * *

UNITED STATES PATENT AND TRADEMARK OFFICE
CERTIFICATE OF CORRECTION

PATENT NO. : 6,423,870 B1
DATED : July 23, 2002
INVENTOR(S) : Michel Langlois et al.

It is certified that error appears in the above-identified patent and that said Letters Patent is hereby corrected as shown below:

Title page,
Item [57], ABSTRACT, remove "The invention is useful for preparing medicines." and replace with -- and medicinal products containing the same which are useful in treating or in preventing melatoninergic disorders. --.

Column 67,
Line 30, insert -- selected from those -- after "A compound".

Column 68,
Line 25, "halogen or linear" should be -- halogen, linear --.
Lines 30 and 45, remove "(".
Lines 38 and 47, remove ")".
Line 40, remove "from".
Lines 41 and 44, remove "(" and ")".
Line 49, remove "an integer"
Line 67, insert -- , -- after "$COOR_a$".

Column 69,
Line 45, insert -- , -- after "benzamide".

Column 70,
Line 1, remove "formula (I) according to".
Line 63, "halogen or linear" should be -- halogen, linear --.
Line 65, "hydroxy or oxo" should be -- hydroxy, oxo --.

Column 71,
Line 1, remove "(".
Line 9, remove ")".
Line 11, remove "from".
Lines 12 and 15, remove "(" and ")".
Line 20, remove "an integer".
Line 23, insert -- , -- after "$A'_3$".
Line 29, insert -- , -- after "$COOR_a$".

Column 72,
Line 20, "their" should be -- its --.
Line 24, remove "formula (I) according to".

UNITED STATES PATENT AND TRADEMARK OFFICE
CERTIFICATE OF CORRECTION

PATENT NO.   : 6,423,870 B1
DATED        : July 23, 2002
INVENTOR(S)  : Michel Langlois et al.

It is certified that error appears in the above-identified patent and that said Letters Patent is hereby corrected as shown below:

Column 73,
Line 28, "halogen or linear" should be -- halogen, linear --.
Line 30, insert -- , -- after "hydroxy".
Line 34, remove "(".
Line 42, remove ")".
Line 44, remove "from".
Lines 45 and 49, remove "(" and ")".
Line 55, remove "an integer".

Column 74,
Line 42, "their" should be -- its --.
Lines 44-67, remove "formula (I) according to" and ", their enantiomers and diastereoisomers, and additional salts thereof with a pharmaceutically acceptable acid or base"

Column 75, line 3 - Column 76, line 9,
Remove "formula (I) according to" and ", their enantiomers and diastereoisomers, and additional salts thereof with a pharmaceutically acceptable acid or base"

Column 76,
Line 10-20, remove "formula (I) according to" and ", their enantiomers and diastereoisomers, and additional salts thereof with a pharmaceutically acceptable acid or base"
Lines 30-67, "Compounds of formula (I) according to claim 1 which are" should be -- A compound of claim 1 which is selected from --.

Column 78,
Line 8, "Compounds of formula (I) according to claim 1 which are" should be -- A compound of claim 1 which is selected from --.

UNITED STATES PATENT AND TRADEMARK OFFICE
CERTIFICATE OF CORRECTION

PATENT NO. : 6,423,870 B1
DATED : July 23, 2002
INVENTOR(S) : Michel Langlois et al.

It is certified that error appears in the above-identified patent and that said Letters Patent is hereby corrected as shown below:

<u>Column 78,</u>
Claim 29, "Compounds of formula (I) according to claim 1 which are" should be
-- A compound of claim 1 which is selected from --.
Line 13, insert -- a -- after "with".
Line 14, "disorders" should be -- disorder --.
Line 16, "claims 1 to 29" should be -- claim 1 --.
Line 17, "condition" should be -- disorder --.
Lines 20 & 29, "as claimed in claims 1 to 29" should be -- of claim 1 --.

Signed and Sealed this

Eighth Day of April, 2003

JAMES E. ROGAN
*Director of the United States Patent and Trademark Office*